United States Patent
Kawa et al.

(10) Patent No.: US 9,072,917 B2
(45) Date of Patent: Jul. 7, 2015

(54) LINEAR ALKYL ESTERS AND THEIR USE IN COSMETIC AND/OR PHARMACEUTICAL COMPOSITIONS

(75) Inventors: Rolf Kawa, Monheim (DE); Stefan Brüning, Düsseldorf (DE); Stefanie Maurer, Mannheim (DE)

(73) Assignee: Cognis IP Management GmbH, Duesseldorf (DE)

( * ) Notice: Subject to any disclaimer, the term of this patent is extended or adjusted under 35 U.S.C. 154(b) by 47 days.

(21) Appl. No.: 13/380,552

(22) PCT Filed: Jun. 19, 2010

(86) PCT No.: PCT/EP2010/003713
§ 371 (c)(1),
(2), (4) Date: Dec. 23, 2011

(87) PCT Pub. No.: WO2011/000489
PCT Pub. Date: Jan. 6, 2011

(65) Prior Publication Data
US 2012/0100197 A1   Apr. 26, 2012

(30) Foreign Application Priority Data

Jun. 20, 2009 (DE) .......................... 10 2009 031 280
Aug. 8, 2009 (EP) ..................................... 09010268
Nov. 26, 2009 (DE) .......................... 10 2009 055 869

(51) Int. Cl.
*A61Q 19/00* (2006.01)
*A61Q 17/04* (2006.01)
*A61K 8/02* (2006.01)
*A61K 8/37* (2006.01)
*A61K 47/14* (2006.01)
*C07C 69/24* (2006.01)
*C07C 69/26* (2006.01)

(52) U.S. Cl.
CPC ................ *A61Q 19/00* (2013.01); *A61Q 17/04* (2013.01); *A61K 8/0208* (2013.01); *A61K 47/14* (2013.01); *C07C 69/24* (2013.01); *A61K 8/37* (2013.01); *C07C 69/26* (2013.01)

(58) Field of Classification Search
None
See application file for complete search history.

(56) References Cited

U.S. PATENT DOCUMENTS

| | | | |
|---|---|---|---|
| 5,609,854 | A | 3/1997 | Guerrero et al. |
| 6,793,929 | B2 | 9/2004 | Bleckmann et al. |
| 2003/0191244 | A1 | 10/2003 | Yu |
| 2004/0109831 | A1* | 6/2004 | Dodwell ........................ 424/59 |
| 2008/0233067 | A1 | 9/2008 | Lee et al. |
| 2008/0241204 | A1* | 10/2008 | Leikauf ......................... 424/402 |
| 2009/0182046 | A1* | 7/2009 | Dierker et al. ................. 514/547 |
| 2009/0202461 | A1 | 8/2009 | Rodriguez et al. |

FOREIGN PATENT DOCUMENTS

| | | |
|---|---|---|
| CN | 1223300 | 7/1999 |
| CN | 101141944 | 3/2008 |
| DE | 10340412 | 4/2005 |
| DE | 102007055595 | 5/2009 |
| EP | 0271139 | 6/1988 |
| EP | 0709083 | 5/1996 |
| EP | 0923935 | 6/1999 |
| EP | 1055424 | 11/2000 |
| EP | 2147954 | 1/2010 |
| FR | 2871689 | 12/2005 |
| JP | S63-154640 | 6/1988 |
| JP | H01-294650 | 11/1989 |
| JP | H03-008110 | 1/1991 |
| JP | H08-239316 | 9/1996 |
| JP | H08-333219 | 12/1996 |
| JP | H09-227383 | 9/1997 |
| JP | H10-504302 | 4/1998 |
| JP | H10-237759 | 9/1998 |

(Continued)

OTHER PUBLICATIONS

Apps, P. J. et al., "Volatile Components of Anal Gland Secretion of Aardworf (*Proteles cristatus*)", Journal of Chemical Ecology, vol. 15, No. 5, 1989, 8 pgs.
Goldberg, Michel et al., "Water activity as a key parameter of synthesis reactions: The example of lipase in biphasic (liquid/solid) media", Enzyme Microb. Technol. vol. 12 Dec. 1990, 976-981.
PCT International Search Report in PCT/EP2010/003713, mailed Apr. 26, 2011, 5 pgs.
Chang, Rey-Chang et al., "Synthesis of Fatty Acid Esters by Recombinant *Staphylococcus epidermidis* lipases in Aqueous Environment", XP-002613921, 2001, 1 pg.
Chowdary, G. V. et al., "Enzymatic synthesis of ethyl hexanoate by transesterification", XP-002613918, 2003, 1 pg.
Goosen, Andre et al., "Autoxidationof nonane and decane: a product study", XP-002613917, 1994, 1 pg.

(Continued)

*Primary Examiner* — Bethany Barham
*Assistant Examiner* — Barbara Frazier
(74) *Attorney, Agent, or Firm* — Servilla Whitney LLC

(57) ABSTRACT

The invention relates to esters of general formula (I) $R_1$—C(=O)—O—$R_2$, wherein (1) $R_1$ represents a linear alkyl radical having 7 to 9 carbon atoms and $R_2$ represents a linear alkyl radical having 9 to 10 carbon atoms or (2) $R_1$ is a linear alk radical having 8 to 9 carbon atoms and $R_2$ is a linear alkyl radical having 8 carbon atoms, or (3) $R_1$ is a linear alkyl radical having 7 to 9 carbon atoms and $R_2$ is a linear alkyl radical having 7 carbon atoms, or (4) $R_1$ is an alkyl radical having 7 or 8 carbon atoms and $R_2$ is an alkyl radical having 9 carbon atoms where, if $R_1$ is a linear alkyl radical, $R_2$ is a branched alkyl radical, or, if $R_1$ is a branched alkyl radical, $R_2$ is a linear alkyl radical or (5) $R_1$ represents an alkyl radical having 8 carbon atoms and $R_2$ is an alkyl radical having 8 carbon atoms, where, if $R_1$ is a linear alkyl radical, $R_2$ is a branched alkyl radical, or, if $R_1$ is a branched alkyl radical, $R_2$ is a linear alkyl radical, or n-octyl isooctanoate, n-decyl isooctanoate, n-decyl isononanoate, isononyl n-decanoate, n-heptyl n-dodecanoate or isononyl isooctanoate.

9 Claims, No Drawings

(56) References Cited

FOREIGN PATENT DOCUMENTS

| | | |
|---|---|---|
| JP | H11-071249 | 3/1999 |
| JP | H11-310741 | 11/1999 |
| JP | 2000-212046 | 8/2000 |
| JP | 2000-212049 | 8/2000 |
| JP | 2002-193740 | 7/2002 |
| JP | 2002-532581 | 10/2002 |
| JP | 2003-137758 | 5/2003 |
| JP | 2003-238484 | 8/2003 |
| JP | 2003-300930 | 10/2003 |
| JP | 2006-020526 | 1/2006 |
| JP | 2006-028180 | 2/2006 |
| JP | 2006-282662 | 10/2006 |
| JP | 2007-509025 | 4/2007 |
| JP | 2008-509288 | 3/2008 |
| JP | 2008-533070 | 8/2008 |
| JP | 2008-542425 | 11/2008 |
| JP | 2010-100590 | 5/2010 |
| WO | WO-95/00107 | 1/1995 |
| WO | WO-96/04884 | 2/1996 |
| WO | WO-99/06021 | 2/1999 |
| WO | WO 00/35968 | 6/2000 |
| WO | WO-2005/042681 | 5/2005 |
| WO | WO-2006/010087 | 1/2006 |
| WO | WO-2006/097235 | 9/2006 |
| WO | WO-2008/130040 | 10/2008 |
| WO | WO-2009/001085 | 12/2008 |
| WO | WO-2010/014655 | 2/2010 |

OTHER PUBLICATIONS

Ruschgen, M. et al., "Symmetrical Wax Esters by One-Step $Re_2O_7$-Catalyzed Oxidation of Fatty Alchohols with Hydrogen Peroxide", *Fat Sci. Technol.* 1995, 250-252.

Sayama, Shinsei et al., "Esterification of aldehydes and alcohols with pyridinium hydrobromide perbromide in water", XP-002613919, 2004, 1 pg.

Xu, Yan et al., "Process for synthesizing ester catalyzed by lipase of *Rhizopus chinensis*", XP-002613920, 2000, 1 pg.

Yus, M. et al., "Carboxylic acid esters: synthesis from organometallic compounds, alkyl halides, primary alcohols, or esters (excluding reactions with carboxylic acid derivatives)", XP-002613922 2007, 1 pg.

Vollhardt, K. Peter C. et al., "Organic Chemistry Structure and Function 4th Edition", *W. H. Freeman and Company*, New York First Printing 2002, 3 pgs.

\* cited by examiner

LINEAR ALKYL ESTERS AND THEIR USE IN COSMETIC AND/OR PHARMACEUTICAL COMPOSITIONS

CROSS REFERENCE TO RELATED APPLICATIONS

This application is a National Stage Entry of International Application No. PCT/EP2010/003713, filed Jun. 19, 2010, which claims priority to German Patent Application No. 102009031280.3, filed Jun. 30, 2009, European Patent Application No. 09010268.2, filed Aug. 8, 2009, and German Patent Application No. 102009055869.1, filed Nov. 26, 2009, each of which is incorporated herein by reference in its entirety.

FIELD OF THE INVENTION

The invention relates to esters and to their use in cosmetic and/or pharmaceutical preparations and to processes for their production.

BACKGROUND OF THE INVENTION

In the field of cosmetic emulsions for skincare and haircare, a large number of requirements are imposed by the consumer: apart from the cleaning and care effects, which determine the intended use, value is placed on such diverse parameters as the highest possible dermatological compatibility, good refatting properties, elegant appearance, optimum sensory impression and storage stability.

Preparations which are used for the cleaning and care of human skin and hair generally comprise, as well as a series of surface-active substances, in particular oil bodies and water. The oil bodies/emollients used are, for example, hydrocarbons, ester oils and also vegetable and animal oils/fats/waxes. In order to satisfy the high market requirements with regard to sensory properties and optimum dermatological compatibility, new oil bodies and emulsifier mixtures are being continually developed and tested. The use of ester oils in cosmetics has been known for a long time. Due to their importance, new processes for producing them are also continuously being developed.

SUMMARY OF THE INVENTION

In one embodiment the present invention to provides novel ester oils, which are typically liquid at 20° C., for cosmetic and/or pharmaceutical applications which, in terms of the sensory properties (lightness, "non-greasy skin feel", softness, spreadability, absorption, distributability, oiliness), have an improved profile and can be incorporated into a large number of cosmetic and/or pharmaceutical formulations. In this connection, the hydrolysis stability of the esters and also the formulatability of the esters at low pH were also of interest. Furthermore, the esters should be incorporable both into W/O and into O/W formulations. Furthermore, the esters should be compatible in particular with crystalline UV filters, pigments, antiperspirant salts and silicones. Furthermore, the esters should be oxidation-stable. Furthermore, especially for preparations of decorative cosmetics (for example make-up), the so-called "non-transfer" property is of interest. Additionally, the compatibility of the esters with preparations which comprise washing-active substances (such as e.g. shower baths, shampoos, hair conditioners) is of interest. It was also of particular interest to provide substances which can completely or partly replace silicone oil in cosmetic and/or pharmaceutical preparations. The silicone oils used in the prior art are disadvantageous inter alia on account of their bioaccumulation. It was of particular interest here to provide substances which make it possible to reduce or to avoid the so-called "whitening effect" in cosmetic and/or pharmaceutical preparations. The undesired, so-called "whitening effect" is evident in the form of a white film/smear which becomes visible after applying the cosmetic and/or pharmaceutical preparation to the skin. It was also of particular interest to provide substances which have a low irritation potential (inter alia skin and eyes). WO 2006/097235 describes esters of 2-propylheptanol with linear or branched carboxylic acids. WO 2006/097235 describes the ester of 2-propylheptanol with 2-propylheptanoic acid. In one or more embodiments the esters of the present invention provide esters that are improved compared with the prior art. It has been found that the esters of the present invention achieve the desired improvements.

DETAILED DESCRIPTION OF THE INVENTION

The invention provides esters of the general formula

$$R_1-C(=O)-O-R_2 \tag{I}$$

(1) in which $R_1$ is a linear alkyl radical having 7 to 9 carbon atoms and $R_2$ is a linear alkyl radical having 9 to 10 carbon atoms, or (2) in which $R_1$ is a linear alkyl radical having 8 to 9 carbon atoms and $R_2$ is a linear alkyl radical having 8 carbon atoms, or (3) in which $R_1$ is a linear alkyl radical having 7 to 9 carbon atoms and $R_2$ is a linear alkyl radical having 7 atoms, or (4) in which $R_1$ is an alkyl radical having 7 or 8 carbon atoms and $R_2$ is an alkyl radical having 9 carbon atoms, where, if $R_1$ is a linear alkyl radical, $R_2$ is a branched alkyl radical, or, if $R_1$ is a branched alkyl radical, $R_2$ is a linear alkyl radical or (5) in which $R_1$ is an alkyl radical having 8 carbon atoms and $R_2$ is an alkyl radical having 8 carbon atoms, where, if $R_1$ is a linear alkyl radical, $R_2$ is a branched alkyl radical, or, if $R_1$ is a branched alkyl radical, $R_2$ is a linear alkyl radical, or n-octyl isooctanoate, n-decyl isooctanoate, n-decyl isononanoate, isononyl n-decanoate, n-heptyl n-dodecanoate, isononyl isooctanoate.

The radicals $R_1$ and $R_2$ can be saturated, mono- or polyunsaturated alkyl radicals. In one embodiment of the invention, $R_1$ and/or $R_2$ are a saturated alkyl radical.

The radical $R_1$ is an alkyl radical having 7, 8 or 9 carbon atoms. Accordingly, it is esters of alcohols with octanoic acids ($R_1$=7 carbon atoms), esters of alcohols with nonanoic acids ($R_1$=8 carbon atoms), esters of alcohols with decanoic acids ($R_1$=9 carbon atoms). The radical $R_1$ can be branched or unbranched (linear). Examples of linear radicals $R_1$ are n-heptyl, n-octyl and n-nonyl.

Branched radicals $R_1$ having 7 carbon atoms are referred to as isoheptyl radicals. Examples of isoheptyl radicals are methylhexyl (1-methylhexyl, 2-methylhexyl, 3-methylhexyl, 4-methylhexyl, 5-methylhexyl), ethylpentyl (1-ethylpentyl, 2-ethylpentyl, 3-ethylpentyl or 4-ethylpentyl), propylbutyl (1-propylbutyl, 2-propylbutyl, 3-propylbutyl), dimethylpentyl (such as, for example, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl), trimethylbutyl (such as, for example, 1,1,2-trimethylbutyl, 1,2,3-trimethylbutyl) or methylethylbutyl (such as, for example, 1-methyl-2-ethylbutyl). An exemplary isoheptyl radical $R_1$ is 1-ethylpentyl.

Branched radicals $R_1$ having 8 carbon atoms are referred to as isooctyl radicals. Examples of isooctyl radicals are methylheptyl (1-methylheptyl, 2-methylheptyl, 3-methylheptyl, 4-methylheptyl, 5-methylheptyl, 6-methylheptyl), ethylhexyl (1-ethylhexyl, 2-ethylhexyl, 3-ethylhexyl or 4-ethylhexyl), propylpentyl (1-propyl-pentyl, 2-propylpentyl, 3-propylpentyl), butylbutyl (such as, for example, 1-butylbutyl, 2-butylbutyl or 3-butylbutyl), dimethylhexyl (such as, for example, 1,1-dimethylhexyl, 1,2-dimethylhexyl, 1,3-dimethylhexyl, 1,4-dimethylhexyl, 2,2-dimethylhexyl, 2,3-dimethylhexyl, 2,4-dimethylhexyl), trimethylpentyl (such as, for example, 1,1,2-trimethylpentyl, 1,2,3-trimethylpentyl, 2,4,4-trimethylpentyl) or methylethylpentyl (such as, for example, 1-methyl-2-ethylpentyl). An exemplary isooctyl radical $R_1$ is 2,4,4-trimethylpentyl.

Branched radicals $R_1$ having 9 carbon atoms are referred to as isononyl radicals. Examples of isononyl radicals are methyloctyl (1-methyloctyl, 2-methyloctyl, 3-methyloctyl, 4-methyloctyl, 5-methyloctyl, 6-methyloctyl, 7-methyloctyl), ethylheptyl (1-ethylheptyl, 2-ethylheptyl, 3-ethylheptyl, 4-ethylheptyl, 5-ethylheptyl or 6-ethylheptyl), propylhexyl (1-propylhexyl, 2-propylhexyl, 3-propylhexyl, 4-propylhexyl, 5-propylhexyl), butylpentyl (such as, for example, 1-butylpentyl, 2-butylpentyl or 3-butylpentyl), dimethylheptyl (such as, for example 1,1-dimethyl-heptyl, 1,2-dimethylheptyl, 1,3-dimethylheptyl, 1,4-dimethylheptyl, 2,2-dimethylheptyl, 2,3-dimethylheptyl, 2,4-dimethylheptyl), trimethylhexyl (such as, for example, 1,1,2-trimethylhexyl, 1,2,3-trimethylhexyl, 2-methyl-4,4-dimethylhexyl) or methylethylhexyl (such as, for example, 1-methyl-2-ethylhexyl). Examples of suitable isononyl radicals $R_1$ are trimethylhexyl radicals and 3,5-dimethyl-n-heptyl.

The radical $R_2$ is an alkyl radical having 8, 9 or 10 carbon atoms. Accordingly, it is esters of octanol ($R_2=8$ carbon atoms) with acids, esters of nonanol ($R_2=9$ carbon atoms) with acids, esters of decanol ($R_2=10$ carbon atoms). The radical $R_1$ can be branched or unbranched (linear). Examples of linear radicals $R_2$ are n-octyl, n-nonyl and n-decyl.

Branched radicals $R_2$ having 8 carbon atoms are referred to as isooctyl radicals. Examples of isooctyl radicals are methylheptyl (1-methylheptyl, 2-methylheptyl, 3-methylheptyl, 4-methylheptyl, 5-methylheptyl, 6-methylheptyl), ethylhexyl (1-ethylhexyl, 2-ethylhexyl, 3-ethylhexyl or 4-ethylhexyl), propylpentyl (1-propyl-pentyl, 2-propylpentyl, 3-propylpentyl), butylbutyl (such as, for example, 1-butylbutyl, 2-butylbutyl or 3-butylbutyl), dimethylhexyl (such as, for example, 1,1-dimethylhexyl, 1,2-dimethylhexyl, 1,3-dimethylhexyl, 1,4-dimethylhexyl, 2,2-dimethylhexyl, 2,3-dimethylhexyl, 2,4-dimethylhexyl), trimethylpentyl (such as, for example, 1,1,2-trimethylpentyl, 1,2,3-trimethylpentyl, 2-methyl-4,4-dimethylpentyl) or methylethylpentyl (such as, for example, 1-methyl-2-ethylpentyl). An exemplary isooctyl radical $R_2$ is 2-ethylhexyl.

Branched radicals $R_2$ having 9 carbon atoms are referred to as isononyl radicals. Examples of isononyl radicals are methyloctyl (1-methyloctyl, 2-methyloctyl, 3-methyloctyl, 4-methyloctyl, 5-methyloctyl, 6-methyloctyl, 7-methyloctyl), ethylheptyl (1-ethylheptyl, 2-ethylheptyl, 3-ethylheptyl, 4-ethylheptyl, 5-ethylheptyl or 6-ethylheptyl), propylhexyl (1-propylhexyl, 2-propylhexyl, 3-propylhexyl, 4-propylhexyl, 5-propylhexyl), butylpentyl (such as, for example, 1-butylpentyl, 2-butylpentyl or 3-butylpentyl), dimethylheptyl (such as, for example, 1,1-dimethylheptyl, 1,2-dimethylheptyl, 1,3-dimethylheptyl, 1,4-dimethylheptyl, 2,2-dimethylheptyl, 2,3-dimethylheptyl, 2,4-dimethylheptyl), trimethylhexyl (such as, for example, 1,1,2-trimethylhexyl, 1,2,3-trimethylhexyl, 2,4,4-trimethylhexyl, 3,5,5-trimethylhexyl) or methylethylhexyl (such as, for example, 1-methyl-2-ethylhexyl). An exemplary isononyl radical $R_2$ is 3,5,5-trimethylhexyl.

Branched radicals $R_2$ having 10 carbon atoms are referred to as isodecyl radicals. Examples of isodecyl radicals are methylnonyl (1-methyloctyl, 2-methyloctyl, 3-methyloctyl, 4-methyloctyl, 5-methyloctyl, 6-methyloctyl, 7-methyloctyl, 8-methyloctyl), ethyloctyl (1-ethyloctyl, 2-ethyloctyl, 3-ethyloctyl, 4-ethyloctyl, 5-ethyloctyl or 6-ethyloctyl, 7-ethyloctyl), propylheptyl (1-propylheptyl, 2-propylheptyl, 3-propylheptyl, 4-propylheptyl, 5-propylheptyl, 6-propylheptyl), butylhexyl (such as, for example, 1-butylhexyl, 2-butylhexyl, 3-butylhexyl, 4-butylhexyl or 5-butylhexyl), dimethyloctyl (such as, for example, 1,1-dimethyloctyl, 1,2-dimethyloctyl, 1,3-dimethyloctyl, 1,4-dimethyloctyl, 2,2-dimethyloctyl, 2,3-dimethyloctyl, 2,4-dimethyloctyl, 3,5-dimethyloctyl), trimethylheptyl (such as, for example, 1,1,2-trimethylheptyl, 1,2,3-trimethylheptyl, 2-methyl-4,4-dimethylheptyl) or methylethylheptyl (such as, for example, 1-methyl-2-ethylheptyl). Examples of suitable isodecyl radicals $R_2$ are trimethylheptyl radicals and 3,5-dimethyl-n-octyl.

One embodiment of the invention (esters of group (1)) relates to esters of the general formula (I) $R_1$—C(=O)—O—$R_2$, in which $R_1$ is a linear alkyl radical having 7 to 9 carbon atoms and $R_2$ is a linear alkyl radical having 9 to 10 carbon atoms. Preferably, the radicals $R_1$ and/or $R_2$ are saturated alkyl radicals. In one or more embodiments, the invention relates to esters selected from the group consisting of n-nonyl n-octanoate, n-nonyl n-nonanoate, n-nonyl n-decanoate, n-decyl n-octanoate, n-decyl n-nonanoate, n-decyl n-decanoate.

One embodiment of the invention (esters of group (2)) relates to esters of the general formula (I) $R_1$—C(=O)—O—$R_2$, in which $R_1$ is a linear alkyl radical having 8 to 9 carbon atoms and $R_2$ is a linear alkyl radical having 8 carbon atoms. Preferably, the radicals $R_1$ and/or $R_2$ are saturated alkyl radicals. One or more of the embodiments of the invention relate to esters selected from the group consisting of n-octyl n-nonanoate and n-octyl n-decanoate.

One embodiment of the invention (esters of group (3)) relates to esters of the general formula (I) $R_1$—C(=O)—O—$R_2$, in which $R_1$ is a linear alkyl radical having 7 to 9 carbon atoms and $R_2$ is a linear alkyl radical having 7 atoms. Preferably, the radicals $R_1$ and/or $R_2$ are saturated alkyl radicals. In one or more embodiments the invention relates to esters selected from the group consisting of n-heptyl n-octanoate, n-heptyl n-nonanoate, n-heptyl n-decanoate.

Esters in which both $R_1$ and $R_2$ are a linear radical are suitable in particular for sensorily demanding formulations in which lightness, "non-greasy skin feel", softness, spreadability, absorption, distributability, oiliness are of importance.

One embodiment of the invention (esters of group (4)) relates to esters of the general formula (I) $R_1$—C(=O)—O—$R_2$, in which $R_1$ is an alkyl radical having 7 or 8 carbon atoms and $R_2$ is an alkyl radical having 9 carbon atoms, where, if $R_1$ is a linear alkyl radical, $R_2$ is a branched alkyl radical, or if $R_1$ is a branched alkyl radical, $R_2$ is a linear alkyl radical. The radicals $R_1$ and/or $R_2$ may be saturated alkyl radicals. One or more embodiments of the invention relate to esters selected from the group consisting of n-nonyl isooctanoate, isononyl n-octanoate, n-nonyl isononanoate, isononyl n-nonanoate. For example, the esters may be selected from the group consisting of n-nonyl-2-ethylhexanoate, 3,5,5-trimethylhexyl n-octanoate, n-nonyl 3,5,5-trimethylhexanoate, 3,5,5-trimethylhexyl n-nonanoate.

One embodiment of the invention (esters of group (5)) relates to esters of the general formula (I) $R_1$—C(=O)—O—

$R_2$, in which $R_1$ is an alkyl radical having 8 carbon atoms and $R_2$ is an alkyl radical having 8 carbon atoms, where, if $R_1$ is a linear alkyl radical, $R_2$ is a branched alkyl radical, or if $R_1$ is a branched alkyl radical, $R_2$ is a linear alkyl radical. Preferably, the radicals $R_1$ and/or $R_2$ are saturated alkyl radicals. One or more embodiments of the invention relate to esters selected from the group consisting of n-octyl isononanoate and isooctyl n-nonanoate. For example, esters may be selected from the group consisting of n-octyl 3,5,5-trimethylhexanoate and 2-ethylhexyl n-nonanoate.

One embodiment of the invention relates to esters of the general formula (I), selected from n-octyl isooctanoate, n-decyl isooctanoate, n-decyl isononanoate, isononyl n-decanoate, n-heptyl n-dodecanoate, isononyl isooctanoate. In one or more embodiments, the esters are selected from the group consisting of n-octyl 2-ethylhexanoate, n-decyl 2-ethylhexanoate, n-decyl 3,5,5-trimethylhexanoate, 3,5,5-trimethylhexyl n-decanoate, n-heptyl n-dodecanoate, 3,5,5-trimethylhexyl 2-ethylhexanoate.

Surprisingly, esters according to the invention are particularly well suited for cosmetic and/or pharmaceutical formulations, in particular for formulations in which a "light" skin feel is important. The esters can be incorporated very easily into a variety of formulations. They have a sensory profile which is comparable with that of volatile silicones, such as, for example, cyclomethicones. Depending on chain length and branching, liquid substances or substance mixtures are obtained which are correspondingly suitable as oil bodies or consistency regulators which give bodies in emulsions. The esters exhibit high stability towards oxidation and hydrolysis. On account of their sensory potential, they are suitable in particular as a partial or complete silicone replacement. On account of their good ability to dissolve UV photoprotective filters, they are suitable in particular as solubility promoters, in particular for UV photoprotective filters, and also as dispersants for solids (powders). According to the invention, it is possible to use a single ester or any desired mixture of different esters.

Preparation Processes

The invention further provides a process for the preparation of the esters of the general formula (I) according to the invention, in which a mixture comprising the corresponding acid and the corresponding alcohol is reacted. In one embodiment of the invention, the mixture comprising the corresponding acid and the corresponding alcohol is reacted with the addition of an esterification catalyst.

In a specific embodiment, the mixture comprising the corresponding acid and the corresponding alcohol is heated, the water which is formed is continuously led away and the crude product is then distilled. The process can be carried out with the addition of an esterification catalyst, e.g. with acid or base catalysis. In one embodiment, the process is carried out without the addition of solvents, such as with starting materials which are as anhydrous as possible. In yet another embodiment of the process, a tin catalyst is used. Suitable tin catalysts are, for example, tin oxalate (e.g. Fascat® 2001), tin oxide (SnO, Fascat® 2000), and tin IV catalysts such as dibutyltin diacetate Fascat® 4200), dibutyltin oxide (Fascat® 4201), and dibutyltin laurate (Fascat® 4202) or tin oxide (SnO), which were formerly marketed by Atofina and are currently marketed by Arkema. The esterification is typically carried out at temperatures between 100-300° C., in particular 200-250° C.

In a further embodiment, at least one enzyme is used as catalyst. Suitable enzymes are all enzymes or enzyme mixtures known to the person skilled in the art which are able to catalyze the esterification of alcohol and acid, examples being lipases, acyl transferases and esterases. The enzymatically catalyzed esterification is usually carried out at temperatures from 20 to 100° C., for example 40 to 80° C.

The esters according to the invention can also be prepared by reacting an alkyl ester of the corresponding acid (e.g. methyl ester or butyl ester) and the corresponding alcohol with the addition of a transesterification catalyst. In such a process, the mixture comprising the alkyl ester of the corresponding acid and the corresponding alcohol is heated with the addition of the esterification catalyst, the water which is formed is continuously led away and the crude product is then distilled. In a specific embodiment, the process is carried out without the addition of solvents, such as with starting materials which are as anhydrous as possible. The esterification is typically carried out at temperatures between 100-300° C., for example 200-250° C. Transesterification catalysts which can be used are all transesterification catalysts known to the person skilled in the art, for example sodium methylate or tetraalkyl titanate as transesterification catalyst.

At least one enzyme can also be used as catalyst. Suitable enzymes are all enzymes or enzyme mixtures known to the person skilled in the art which are able to catalyze the transesterification of alcohol and acid methyl ester, examples being lipases, acyl transferases and esterases. The enzymatically catalyzed esterification is usually carried out at temperatures from 20 to 100° C., for example 40 to 80° C.

The invention encompasses both individual esters and also mixtures of different esters.

Cosmetic/Pharmaceutical Preparations

The esters according to the invention allow the production of stable cosmetic and pharmaceutical preparations, in particular emulsions with a particularly light skin feel.

The invention further provides the use of the esters as described herein in cosmetic and/or pharmaceutical preparations. The esters are suitable in particular as oil bodies and/or as solubility promoters and/or as dispersants in cosmetic and/or pharmaceutical preparations.

The invention further provides the use of the esters as claimed in claim 1 for producing cosmetic and/or pharmaceutical preparations.

The invention further provides in particular the use of the esters as described herein in cosmetic and/or pharmaceutical preparations for the wetting or impregnation or coating of utility wipes and/or hygiene wipes which are used for cleaning the body and/or for bodycare.

The present invention further provides cosmetic and/or pharmaceutical preparations comprising 0.1 to 95% by weight of an ester as described herein.

The present invention further provides cosmetic and/or pharmaceutical preparations comprising
  (a) at least one ester as described herein
  (b) at least one interface-active substance (b-1) and/or wax component (b-2) and/or polymer (b-3) and/or a further oil body (b-4).

The present invention further provides cosmetic and/or pharmaceutical preparations comprising
  (a) at least one ester as described herein
  (d) at least one UV photoprotective filter.

Certain embodiments of the cosmetic and/or pharmaceutical preparations comprise:
  (a) at least one ester selected from the group consisting of the group which is formed from n-nonyl n-octanoate, n-nonyl n-nonanoate, n-nonyl n-decanoate, n-decyl n-octanoate, n-decyl n-nonanoate, n-decyl n-decanoate, n-octyl n-nonanoate, n-octyl n-decanoate, n-heptyl n-octanoate, n-heptyl n-nonanoate, n-heptyl n-decanoate, n-nonyl isooctanoate, (in particular n-nonyl 2-ethylhexanoate), isononyl n-octanoate (in particular 3,5,5-trimethylhexyl n-octanoate), n-nonyl isononanoate (in particular n-nonyl 3,5,5-trimethylhexanoate), isononyl n-nonanoate (in particular 3,5,5-trimethylhexyl n-nonanoate), n-octyl isononanoate (in particular n-octyl 3,5,5-trimethylhexanoate), isooctyl n-nonanoate (in particular 2-ethylhexyl n-nonanoate), n-octyl isooctanoate (in particular n-octyl 2-ethylhexanoate), n-decyl isooctanoate (in particular n-decyl 2-ethylhexanoate), n-decyl isononanoate (in particular n-decyl 3,5,5-trimethylhexanoate), isononyl n-decanoate (in particular 3,5,5-trimethylhexyl n-decanoate), n-heptyl n-dodecanoate, isononyl isooctanoate (in particular 3,5,5-trimethylhexyl 2-ethylhexanoate).

(b) at least one emulsifier (b-1) and/or surfactant (b-2) and/or wax component (b-3) and/or polymer (b-4) and/or a further oil body (b-5).

Preparations according to the invention may comprise 0.1 to 95% by weight, 0.2 to 80% by weight, 0.5 to 70% by weight, 0.75 to 60% by weight, 1 to 50% by weight, or 1-40% by weight, of at least one ester (a).

The invention further provides preparations cosmetic and/or pharmaceutical preparations comprising
a) 0.1-95% by weight, 0.2 to 80% by weight, 0.1 to 70% by weight, 0.1 to 60% by weight, 0.1 to 50% by weight, or 0.1-40% by weight, of at least one ester as described herein,
b) 0.1-20% by weight of interface-active substance (b-1) and/or wax component (b-2) and/or polymer (b-3), 0.1-40% by weight of further oil bodies (b-4) and
c) 0-98% by weight of water.

The preparations according to the invention may comprise at least 0.1, at least 0.5, at least 0.75, at least 1, or at least 5% by weight, of one or more esters as described herein.

All % by weight data refer to % by weight based on the cosmetic and/or pharmaceutical preparations.

In one embodiment of the invention, the preparations comprise at least one ester selected from the group consisting of n-nonyl n-octanoate, n-nonyl n-nonanoate, n-nonyl n-decanoate, n-decyl n-octanoate, n-decyl n-nonanoate, n-decyl n-decanoate, n-octyl n-nonanoate, n-octyl n-decanoate, n-heptyl n-octanoate, n-heptyl n-nonanoate, n-heptyl n-decanoate, n-nonyl isooctanoate (in particular n-nonyl 2-ethylhexanoate), isononyl n-octanoate (in particular 3,5,5-trimethylhexyl n-octanoate), n-nonyl isononanoate (in particular n-nonyl 3,5,5-trimethylhexanoate), isononyl n-nonanoate (in particular 3,5,5,-trimethylhexyl n-nonanoate), n-octyl isononanoate (in particular n-octyl 3,5,5-trimethylhexanoate), isooctyl n-nonanoate (in particular 2-ethylhexyl n-nonanoate), n-octyl isooctanoate (in particular n-octyl 2-ethylhexanoate), n-decyl isooctanoate (in particular n-decyl 2-ethylhexanoate), n-decyl isononanoate (in particular n-decyl 3,5,5-trimethylhexanoate), isononyl n-decanoate (in particular 3,5,5-trimethylhexyl n-decanoate), n-heptyl n-dodecanoate, isononyl isooctanoate (in particular 3,5,5-trimethylhexyl 2-ethylhexanoate) or any desired mixtures thereof.

The preparations according to the invention, and also the esters according to the invention are suitable to be incorporated as a basis in all cosmetic compositions for bodycare and body cleaning, such as e.g. body oil, baby oil, body milk, creams, lotions, sprayable emulsions, sunscreen compositions, antiperspirants, liquid and bar soaps etc. They can also be used in surfactant-containing formulations such as e.g. foam baths and shower baths, hair shampoos and care rinses. They can be applied as care component on tissues, papers, wipes, nonwoven products, sponges, puffs, plasters and bandages which are used in the field of hygiene and care (wet wipes for baby hygiene and babycare, cleansing wipes, face cleansing wipes, skincare wipes, care wipes with active ingredients to combat skin aging, wipes with sunscreen formulations and insect repellents, and also wipes for decorative cosmetics or for after-sun treatment, toilet wet wipes, antiperspirant wipes, diapers, tissues, wet wipes, hygiene products, self-tanning wipes). They can also be used inter alia in preparations for haircare, hair cleansing or hair coloring. They can furthermore be used in preparations of decorative cosmetics, such as, for example, lipsticks, lip gloss, make-up, foundations, powders, eyeshadows, mascara and the like.

Depending on the application purpose, the cosmetic formulations comprise a series of further auxiliaries and additives, such as, for example, surfactants, further oil bodies, emulsifiers, pearlescent waxes, consistency regulators, thickeners, super fatting agents, stabilizers, polymers, fats, waxes, lecithins, phospholipids, biogenic active ingredients UV photoprotective factors, antioxidants, deodorants, antiperspirants, antidandruff agents, film formers, swelling agents, insect repellents, self-tanning agents, tyrosine inhibitors (depigmentation agents), fillers, hydrotropes, solubilizers, preservatives, perfume oils, dyes etc., which are listed below by way of example.

Interface-Active Substance b-1)

In one embodiment of the invention, the preparations according to the invention comprise at least one interface-active substance. The compositions according to the invention comprise the interface-active substance(s) in an amount of from 0 to 80% by weight, 0 to 40% by weight, 0.1 to 20% by weight, 0.1 to 15% by weight or 0.1 to 10% by weight, based on the total weight of the composition.

Suitable interface-active substances are in principle any substance which lowers the surface tension between the aqueous phase and the nonaqueous phase. Interface-active substances include emulsifiers and surfactants. In one embodiment of the invention, the preparation according to the invention comprises more than one interface-active substance. The person skilled in the art uses customary systems (such as e.g. emulsifier and coemulsifier) depending on the other components. A suitable emulsifier is in principle any interface-active substance, but in particular substances with an HLB value of from 1 to 20 on the Griffin scale. Each emulsifier is assigned a so-called HLB value (a dimensionless number between 1 and 20, Griffin scale), which indicates whether a preferential water solubility or oil solubility is present. Numbers below 9 characterize preferentially oil-soluble, hydrophobic emulsifiers, numbers above 11 water-soluble, hydrophilic emulsifiers. The HLB value says something about the balance between the size and strength of the hydrophilic and lipophilic groups of an emulsifier. The Griffin scale is described in W C Griffin, J. Soc. Cosmet. Chem. 1 (1949) 311; W C Griffin, J. Soc. Cosmet. Chem. 5 (1954) 249.

The HLB value of an emulsifier can be calculated from increments, where the HLB increments for the different hydrophilic and hydrophobic groups from which a molecule is composed can be found in tabular works (e.g. H. P. Fiedler, Lexikon der Hilfsstoffe für Pharmazie, Kosmetik and angrenzende Gebiete [Lexicon of Auxiliaries for Pharmacy, Cosmetics and related fields], Editio Cantor Verlag, Aulendorf, $4^{th}$ edition 1996) or in information from manufacturers. The solubility of the emulsifier in the two phases in practice determines the type of emulsion. If the emulsifier is more soluble in water, this gives an O/W emulsion. By contrast, if the emulsifier has better solubility in the oil phase, under otherwise identical preparation conditions, a W/O emulsion is formed.

Nonionic Emulsifiers

The group of nonionic emulsifiers includes, for example:
(1) addition products of from 2 to 50 mol of ethylene oxide and/or 1 to 20 mol of propylene oxide onto linear fatty alcohols having 8 to 40 carbon atoms, onto fatty acids having 12 to 40 carbon atoms and onto alkylphenols having 8 to 15 carbon atoms in the alkyl group.
(2) $C_{12}$-$C_{18}$-fatty acid mono- and diesters of addition products of from 1 to 50 mol of ethylene oxide onto glycerol.
(3) Sorbitan mono- and diesters of saturated and unsaturated fatty acids having 6 to 22 carbon atoms and their ethylene oxide addition products.
(4) Alkyl mono- and oligoglycosides having 8 to 22 carbon atoms in the alkyl radical and their ethoxylated analogs.
(5) Addition products of from 7 to 60 mol of ethylene oxide onto castor oil and/or hydrogenated castor oil.
(6) Polyol esters, and in particular polyglycerol esters, such as e.g. polyol poly-12-hydroxystearate, polyglycerol polyricinoleate, polyglyceryl-4 laurate, polyglycerol diisostearate or polyglycerol dimerate. Likewise of suitability are mixtures of compounds of two or more of these substance classes, such as e.g. polyglyceryl-4 diisostearate/polyhydroxystearate/sebacate.
(7) Addition products of from 2 to 15 mol of ethylene oxide onto castor oil and/or hydrogenated castor oil.
(8) Partial esters based on linear, branched, unsaturated or saturated $C_6$-$C_{22}$-fatty acids, ricinoleic acid, and 12-hydroxystearic acid and polyglycerol, pentaerythritol, dipentaerythritol, sugar alcohols (e.g. sorbitol), alkyl glucosides (e.g. methyl glucoside, butyl glucoside, lauryl glucoside), and polyglucosides (e.g. cellulose), or mixed esters, and also sucrose polystearate (commercially available as Emulgade® SUCRO, Cognis GmbH).
(9) Polysiloxane-polyalkyl-polyether copolymers and corresponding derivatives.
(10) Mixed esters of pentaerythritol, fatty acids, citric acid and fatty alcohol and/or mixed esters of fatty acids having 6 to 22 carbon atoms, methyl glucose and polyols, such as glycerol or polyglycerol.

The addition products of ethylene oxide and/or of propylene oxide onto fatty alcohols, fatty acids, alkylphenols, glycerol mono- and diesters, and also sorbitan mono- and diesters of fatty acids or onto castor oil are known, commercially available products. These are homolog mixtures whose average degree of alkoxylation corresponds to the ratio of the quantitative amounts of ethylene oxide and/or propylene oxide and substrate with which the addition reaction is carried out. Depending on the degree of ethoxylation, they are W/O or O/W emulsifiers. $C_{12/18}$-Fatty acid mono- and diesters of addition products of ethylene oxide onto glycerol are known as refatting agents for cosmetic preparations.

Particularly well suited and mild emulsifiers according to the invention are polyol poly-12-hydroxystearate and mixtures thereof, which are sold, for example, under the trade names "Dehymuls® PGPH" (W/O emulsifier) or "Eumulgin® VL 75" (mixture with coco glucosides in the weight ratio 1:1, O/W emulsifier) or Dehymuls® SBL (W/O emulsifier) by Cognis Deutschland GmbH. In this connection, reference may be made in particular to the European patent EP 766 661 B1. The polyol component of these emulsifiers can be derived from substances which have at least two, for example 3 to 12 or 3 to 8, hydroxyl groups and 2 to 12 carbon atoms.

Suitable lipophilic W/O emulsifiers are in principle emulsifiers with an HLB value from 1 to 8, which are summarized in numerous tabular works and are known to the person skilled in the art. Some of these emulsifiers are listed, for example, in Kirk-Othmer, Encyclopedia of Chemical Technology, $3^{rd}$ edition, 1979, volume 8, page 913. For ethoxylated products, the HLB value can also be calculated according to the following formula: HLB=(100−L):5, where L is the weight fraction of the lipophilic groups, i.e. of the fatty alkyl or fatty acyl groups in percent by weight, in the ethylene oxide adducts.

From the group of W/O emulsifiers, partial esters of polyols, in particular of $C_4$-$C_6$-polyols, are particularly advantageous, such as, for example, partial esters of pentaerythritol or sugar esters, e.g. sucrose distearate, sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan mono hydroxystearate, sorbitan sesquihydroxystearate, sorbitan di hydroxystearate, sorbitan tri hydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Suitable emulsifiers are also addition products of from 1 to 30, for example 5 to 10, mol of ethylene oxide onto the specified sorbitan esters.

Depending on the formulation, it may be advantageous to additionally use at least one emulsifier from the group of nonionic W/O emulsifiers (HLB value: 8-18) and/or solubilizers. These are, for example, the ethylene oxide adducts already mentioned in the introduction and having a correspondingly high degree of ethoxylation, e.g. 10-20 ethylene oxide units for O/W emulsifiers and 20-40 ethylene oxide units for so-called solubilizers. Particularly advantageous O/W emulsifiers according to the invention are ceteareth-12, ceteareth-20 and PEG-20 stearate. Suitable solubilizers are include Eumulgin® HRE 40 (INCI: PEG-40 hydrogenated castor oil), Eumulgin® HRE 60 (INCI: PEG-60 hydrogenated castor oil), Eumulgin® L (INCI: PPG-1-PEG-9 lauryl glycol ether), and Eumulgin® SML 20 (INCI: Polysorbate-20).

Nonionic emulsifiers from the group of alkyl oligoglycosides are particularly skin-friendly and are therefore suitable as O/W emulsifiers. $C_8$-$C_{22}$-Alkyl mono- and oligoglycosides, their preparation and their use are known from the prior art. Their preparation takes place in particular by reacting glucose or oligosaccharides with primary alcohols having 6 to 24, preferably 8 to 22, carbon atoms. As regards the glycoside radical, either monoglycosides, in which one cyclic sugar radical is glycosidically bonded to the fatty alcohol, or oligomeric glycosides with a degree of oligomerization up to about 8, for example, are suitable. The degree of oligomerization here is a statistical average value, which is based on a homolog distribution customary for such technical-grade products. Products which are available under the name Plantacare® or Plantaren® contain a glucosidically bonded $C_8$-$C_{16}$-alkyl group on an oligoglucoside radical, the average degree of oligomerization of which is 1 to 2. The acyl glucamides derived from glucamine are also suitable as nonionic emulsifiers. According to the invention, a product which is sold under the name Emulgade® PL 68/50 by Cognis Deutschland GmbH and is a 1:1 mixture of alkyl polyglucosides and fatty alcohols may be used. According to the invention, it is also advantageously possible to use a mixture of lauryl glucoside, polyglyceryl-2 dipolyhydroxystearate, glycerol and water, which is commercially available under the name Eumulgin® VL 75.

Suitable emulsifiers are also substances such as lecithins and phospholipids. Examples of natural lecithins which may be mentioned are the cephalins, which are also referred to as phosphatidic acids and are derivatives of 1,2-diacyl-sn-glycerol-3-phosphoric acid. By contrast, phospholipids are usually understood as meaning mono- and diesters of phosphoric acid with glycerol (glycerol phosphates), which are generally classified as fats. In addition, sphingosines and/or sphingolipids are also suitable.

As emulsifiers, silicone emulsifiers, for example, may be present. These can be selected, for example, from the group of alkylmethicone copolyols and/or alkyldimethicone copolyols, in particular from the group of the compounds which are characterized by the following chemical structure:

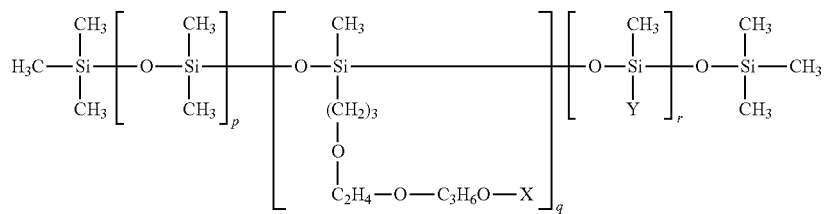

in which X and Y, independently of one another, are selected from the group H (hydrogen) and also the branched and unbranched alkyl groups, acyl groups and alkoxy groups having 1-24 carbon atoms, p is a number from 0-200, q is a number from 1-40, and r is a number from 1-100.

One example of silicone emulsifiers to be used particularly advantageously for the purposes of the present invention are dimethicone copolyols, which are sold by Evonik Goldschmidt under the trade names AXIL® B 8832, ABIL® B 8843, ABIL® B 8847, ABIL® B 8851, ABIL® B 8852, ABIL® B 8863, ABIL® B 8873 and ABIL® B 88183.

Another example of interface-active substances to be used particularly advantageously for the purposes of the present invention is cetyl PEG/PPG-10/1 dimethicone (cetyl dimethicone copolyol), which is sold by Evonik Goldschmidt under the trade name ABIL® EM 90.

A further example of interface-active substances to be used particularly advantageously for the purposes of the present invention is the cyclomethicone dimethicone copolyol, which is sold by Evonik Goldschmidt under the trade name ABIL® EM 97 and ABIL® WE 09.

Furthermore, the emulsifier lauryl PEG/PPG-18/18 methicone (laurylmethicone copolyol) has proven to be very particularly advantageous and is available under the trade name Dow Corning® 5200 Formulation Aid from Dow Corning Ltd. Also advantageous is a silicone emulsifier with the INCI name cyclopentasiloxane and PEG/PG-18-18 dimethicone, which is available, for example, under the trade name Dow Corning® 5225 C Formulation Aid.

A further advantageous silicone emulsifier is octyl dimethicone epoxy glucoside from Wacker. For a water-in-silicone oil emulsion according to the invention, it is possible to use all known emulsifiers used for this type of emulsion. Water-in-silicone emulsifiers which are suitable according to the invention are cetyl PEG/PPG-10/1 dimethicone and lauryl PEG/PPG-18/18 methicone [e.g. ABIL® EM 90 (Evonik Goldschmidt), DC5200 Formulation Aid (Dow Corning)], and any desired mixtures of the two emulsifiers.

A suitable anionic O/W emulsifier is e.g. the product available under the INCI name disodium cetearyl sulfosuccinate (trade name Eumulgin® Prisma, Cognis GmbH).

Surfactants

In one embodiment of the invention, the preparations according to the invention comprise at least one surfactant as interface-active compounds. Interface-active substances which may be present are anionic, nonionic, cationic and/or amphoteric or zwitterionic surfactants. In surfactant-containing cosmetic preparations, such as, for example, shower gels, foam baths, shampoos etc., at least one anionic surfactant may be present.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en) yl oligoglycosides or glucoronic acid derivatives, fatty acid N-alkylglucamaides, protein hydrolyzates (in particular wheat-based vegetable products), polyol fatty acid esters, sugar esters, sorbitan esters, polysorbates and amine oxides. If the nonionic surfactants contain polyglycol ether chains, these can have a conventional homolog distribution, but in certain embodiments have a narrowed homolog distribution.

Zwitterionic surfactants is the term used to refer to those surface-active compounds which carry at least one quaternary ammonium group and at least one —COO$^{(-)}$ or —SO$_3^{(-)}$ group in the molecule. Particularly suitable zwitterionic surfactants are the so-called betaines, such as the N-alkyl-N,N-dimethylammonium glycinates, for example cocoalkyl dimethylammonium glycinate, N-acylaminopropyl-N,N-dimethylammonium glycinates, for example cocoacylaminopropyldimethylammonium glycinate and 2-alkyl-3-carboxylmethyl-3-hydroxyethylimidazoline having in each case 8 to 18 carbon atoms in the alkyl or acyl group, and cocoacylaminoethylhydroxyethylcarboxymethyl glycinate. An exemplary zwitterionic surfactant is the fatty acid amide derivative known under the INCI name Cocoamidopropyl Betaine.

Likewise suitable, especially as cosurfactants, are ampholytic surfactants. Ampholytic surfactants are understood as meaning those surface-active compounds which, apart from a $C_8$-$C_{18}$-alkyl or acyl group in the molecule, contain at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkyliminodipropionic acids (commercially available for example under the trade name Dehyton® DC), N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Exemplary ampholytic surfactants are N-cocoalkylaminopropionate, cocoacylaminoethylaminopropionate and $C_{12-18}$-acylsarcosine. Also suitable are derivatives of N-alkyliminodipropionic acids, such as, for example, N-lauryl-beta-iminopropionates, commercially available under the trade name Deriphat® 160 C. Also suitable are amphoacetates, such as e.g. cocoamphoacetates (e.g. Dehyton® MC) or cocoamphodiacetates (such as e.g. Dehyton® DC).

Anionic surfactants are characterized by a water-solubilizing, anionic group such as e.g. a carboxylate, sulfate, sulfonate, citrate or phosphate group, and a lipophilic radical. Skin-compatible anionic surfactants are known to the person skilled in the art in a large number from relevant textbooks and are commercially available. They are in particular alkylsulfates in the form of their alkali metal, ammonium or alkanolammonium salts, alkyl ether sulfates, alkyl ether carboxylates, acyl isethionates, acyl sarcosinates, acyl taurines with linear alkyl or acyl groups having 12 to 18 carbon atoms, and sulfosuccinates and acyl glutamates in the form of their alkali metal or ammonium salts. Particularly suitable anionic surfactants are glyceryl stearate citrate (as commercially available e.g. under the trade names Imwitor® 370, Imwitor® 372P, Axol® C, 62 or Dracorin® CE 614035) or glyceryl stearate lactate compounds. An example of a suitable alkylsulfate is sodium cetearyl sulfate (trade name Lanette® E), an example of a suitable phosphate is potassium cetyl phosphate (trade name Amphisol® K). An example of a suitable acyl glutamate is sodium stearoyl glutamate (trade name e.g. Eumulgin® SG). A further example of a suitable anionic surfactant is sodium lauryl glucose carboxylate (trade name Plantapon® LGC).

Cationic surfactants which can be used include quaternary ammonium compounds. These include ammonium halides, for example chlorides and bromides, such as alkyltrimethylammonium chlorides, dialkyldimethylammonium chlorides and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Suitable pseudo cationic surfactants are, for example, stearylaminopropyl dimethylamine (commercially available under the trade name Dehyquart® S18 or Incromine® SB or TegoAmide® S18). Furthermore, the very readily biodegradable quaternary ester compounds, such as, for example, the dialkylammonium methosulfates and methylhydroxyalkyldialkoyloxyalkylammonium ethosulfates marketed under the trade name Stepantex® and the corresponding products of the Dehyquart® series can be used as cationic surfactants. The term "ester quats" is generally understood as meaning quaternized fatty acid triethanolamine ester salts. They can impart a particular soft feel to the compositions according to the invention. These are known substances which are prepared by the relevant methods of organic chemistry. Further cationic surfactants that can be used according to the invention are the quaternized protein hydrolyzates. Suitable cationic surfactants are, for example, dipalmitoylethyl hydroxyethylmonium methosulfate (trade name Dehyquart® C4046), distearoylethyl hydroxyethylmonium methosulfate (trade name Dehyquart® F75), dicocoylethyl hydroxyethylmonium methosulfate (trade name Dehyquart® L80), behentrimonium chloride (trade name Varisoft® BT), distearyldimonium chloride (trade name Varisoft® TA 100), palmitamidopropyltrimonium chloride (trade name Varisoft® PATC).

Wax Component b-2)

In one embodiment of the invention, the preparations according to the invention comprise at least one wax component. The compositions according to the invention comprise the wax component(s) in an amount of from 0 to 40% by weight, from 0 to 20% by weight, 0.1 to 15% by weight or from 0.1 to 10% by weight, based on the total weight of the composition.

The term wax is usually understood as meaning all natural or artificially obtained substances and substance mixtures having the following properties: they are of solid to brittley hard consistency, coarse to finely crystalline, transparent to opaque and melt above 30° C. without decomposition. Even a little above the melting point, they are of low viscosity and not thread-drawing and exhibit a strongly temperature-dependent consistency and solubility. According to the invention, it is possible to use one wax component or a mixture of wax components which melt at 30° C. or above.

According to the invention, waxes which can be used are also fats and fat-like substances with wax-like consistency provided they have the required melting point. These include, inter alia, fats (triglycerides), mono- and diglycerides, natural and synthetic waxes, fatty and wax alcohols, fatty acids, esters of fatty alcohols and fatty acids, and also fatty acid amides or any desired mixtures of these substances.

Fats are understood as meaning triacylglycerols, i.e. the triple esters of fatty acids with glycerol. In certain embodiments they contain saturated, unbranched and unsubstituted fatty acid radicals. These may also be mixed esters, i.e. triple esters of glycerol with different fatty acids. Substances which can be used according to the invention and are particularly well suited as consistency regulators are so-called hydrogenated fats and oils which are obtained by partial hydrogenation. Vegetable hydrogenated fats and oils are included e.g. hydrogenated castor oil, peanut oil, soya oil, rapeseed oil, colza seed oil, cotton seed oil, soya oil, sunflower oil, palm oil, palm kernel oil, linseed oil, almond oil, corn oil, olive oil, sesame oil, cocoa butter, shea butter and coconut fat.

Of suitability are, inter alia, the triple esters of glycerol with C12-C60-fatty acids and in particular C12-C36-fatty acids. These include hydrogenated castor oil, a triple ester of glycerol and a hydroxystearic acid, which is commercially available for example under the name Cutina HR. Likewise suitable are glycerol tristearate, glycerol tribehenate (e.g. Syncrowax HRC), glycerol tripalmitate or the triglyceride mixtures known under the name Syncrowax HGLC, with the proviso that the melting point of the wax component or of the mixture is 30° C. or above.

Wax components which can be used according to the invention are in particular mono- and diglycerides or mixtures of these partial glycerides. The glyceride mixtures which can be used according to the invention include the products Novata AB and Novata B (mixture of C12-C18-mono-, di- and triglycerides), and Cutina® HVG (hydrogenated vegetable glycerides) or Cutina® GMS (glyceryl stearate) marketed by Cognis Deutschland GmbH & Co. KG.

The fatty alcohols which can be used according to the invention as wax component include the C12-C50-fatty alcohols. The fatty alcohols can be obtained from natural fats, oils and waxes, such as, for example, myristyl alcohol, 1-pentadecanol, cetyl alcohol, 1-heptadecanol, stearyl alcohol, 1-nonadecanol, arachidyl alcohol, 1-heneicosanol, behenyl alcohol, brassidyl alcohol, lignoceryl alcohol, ceryl alcohol or myricyl alcohol. According to the invention, saturated unbranched fatty alcohols may be used. However, unsaturated, branched or unbranched fatty alcohols can also be used according to the invention as wax component provided they have the required melting point. According to the invention, it is also possible to use fatty alcohol cuts, as are produced during the reduction of naturally occurring fats and oils, such as e.g. beef tallow, peanut oil, colza oil, cotton seed oil, soya oil, sunflower oil, palm kernel oil, linseed oil, castor oil, corn oil, rapeseed oil, sesame oil, cocoa butter and coconut fat. However, it is also possible to use synthetic alcohols, e.g. the linear, even-numbered fatty alcohols of the Ziegler synthesis (alfols) or the partially branched alcohols from the oxo synthesis (dobanols). Included in certain embodiments of the invention are C14-C22-fatty alcohols, which are marketed, for example by Cognis Deutschland GmbH under the name Lanette 16 (C16-alcohol), Lanette 14 (C14-alcohol), Lanette 0 (C16/C18-alcohol) and Lanette 22 (C18/C22-alcohol). Fatty alcohols impart a drier skin feel to the compositions than triglycerides.

Wax components which can be used are also C14-C40-fatty acids or mixtures thereof. These include, for example, myristic acid, pentadecanoic acid, palmitic acid, margaric acid, stearic acid, nonadecanoic acid, arachic acid, behenic acid, lignoceric acid, cerotinic acid, melissic acid, erucic acid and elaeostearic acid, and also substituted fatty acids, such as e.g. 12-hydroxystearic acid, and the amides or monoethanolamides of the fatty acids, this list being exemplary and not limiting in character.

According to the invention, it is possible to use, for example, natural vegetable waxes, such as candelilla wax, carnauba wax, Japan wax, esparto grass wax, cork wax, guaruma wax, rice germ oil wax, sugar cane wax, ouricury wax, montan wax, sunflower wax, fruit waxes, such as orange waxes, lemon waxes, grapefruit wax, bayberry wax and animal waxes, such as e.g. beeswax, shellac wax, spermaceti, wool wax and uropygial grease. Within the context of the invention, it may be advantageous to use hydrogenated or hardened waxes. The natural waxes that can be used according to the invention also include the mineral waxes, such as e.g. ceresine and ozokerite, or the petrochemical waxes, such as e.g. petrolatum, paraffin waxes and microwaxes. As wax component, it is also possible to use chemically modified waxes, in particular the hard waxes, such as e.g. montan ester waxes, sasol waxes and hydrogenated jojoba waxes. The synthetic waxes which can be used according to the invention include, for example, wax-like polyalkylene waxes and polyethylene glycol waxes. Vegetable waxes may be used according to the invention.

The wax component can likewise be selected from the group of wax esters of saturated and/or unsaturated, branched and/or unbranched alkanecarboxylic acids and saturated and/or unsaturated, branched and/or unbranched alcohols, from the group of the esters of aromatic carboxylic acids, dicarboxylic acids, tricarboxylic acids and hydroxycarboxylic acids (e.g. 12-hydroxystearic acid) and saturated and/or unsaturated, branched and/or unbranched alcohols, and also from the group of lactides of long-chain hydroxycarboxylic acids. Examples of such esters are the C16-C40-alkylstearates, C20-C40-alkylstearates (e.g. Kester wax K82H), C20-C40-dialkyl esters of dimer acids, C18-C38-alkyl hydroxystearoylstearates or C20-C40-alkyl erucates. It is also possible to use C30-C50-alkylbeeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetyl ester, cetearyl behenate and behenyl behenate.

Polymers b-3)

In one embodiment of the invention, the preparations according to the invention comprise at least one polymer. The preparations according to the invention comprise the polymer(s) in an amount of from 0 to 20% by weight, 0.05 to 18% by weight, 0.05 to 15% by weight, 0.05 to 10% by weight, or 0.1 to 1% by weight, based on the total weight of the preparations. In certain embodiments of the invention, the preparations according to the invention comprise the polymer(s) in an amount of from 0.1 to 5% by weight, 0.1 to 3% by weight, or 0.1 to 2% by weight, based on the total weight of the preparation.

Suitable cationic polymers are, for example, cationic cellulose derivatives, such as e.g. a quaternized hydroxyethylcellulose, which is available under the name Polymer JR 400® from Amerchol, cationic starch, copolymers of diallylammonium salts and acrylamides, quaternized vinylpyrrolidone/vinylimidazole polymers, such as e.g. Luviquat® (BASF), condensation products of polyglycols and amines, quaternized collagen polypeptides, such as, for example, lauryldimonium hydroxypropyl hydrolyzed collagen (Lamequat® L/Grünau), quaternized wheat polypeptides, polyethyleneimine, cationic silicone polymers, such as e.g. amidomethicones, copolymers of adipic acid and dimethylaminohydroxypropyldiethylenetriamine (Cartaretine®/Sandoz), copolymers of acrylic acid with dimethyldiallylammonium chloride (Merquat® 550/Chemviron), polyaminopolyamides, cationic chitin derivatives such as, for example, quaternized chitosan, optionally in microcrystalline distribution, condensation products of dihaloalkylene, such as e.g. dibromobutane with bisdialkylamines, such as e.g. bisdimethylamino-1,3-propane, cationic guar gum, such as e.g. Jaguar® CBS, Jaguar® C-17, Jaguar® C-16 from Celanese, quaternized ammonium salt polymers, such as e.g. Mirapol® A-15, Mirapol® AD-1, Mirapol® AZ-1 from Miranol.

Suitable anionic, zwitterionic, amphoteric and nonionic polymers are, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked and polyol-crosslinked polyacrylic acids, acrylamidopropyltrimethylammonium chloride/acrylate copolymers, octylacrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinylcaprolactam terpolymers, and optionally derivatized cellulose ethers and silicones.

Suitable anionic polymers include those with the INCI name Carbomer, such as e.g. the carbopol grades 980, 980, 981, 1382, 2984, 5984, and also the products available under the trade names Rheocare® C plus and Rheocare® 400. Further suitable anionic polymers are those with the INCI name Acrylates/C10-30 Alkyl Acrylate Crosspolymer (trade names e.g. Pemulen® TR, Pemulen® TR 2, Carbopol® Ultrez), Acrylates Copolymer (trade names e.g. Rheocare TTA, TTN, TTN-2), Acrylamide/Sodium Acrylate Copolymer (trade names e.g. Cosmedia® ATC), Sodium Polyacrylate (trade names e.g. Cosmedia® ATH, Cosmedia® SP), Polyacrylamides (trade names e.g. Sepigel® 305 or Sepigel® 501). Exemplary anionic polymers are polyacrylic acid homopolymers and copolymers.

Further suitable polymers are silicone elastomer gums, such as e.g. silicone elastomer mixtures, such as e.g. mixtures with the INCI names Cyclopentasiloxane (and) Dimethiconol (and) Dimethicone Crosspolymer (trade name Dow Corning® DC 9027), mixtures with the INCI name Isodecyl neopentanoate (and) Dimethicone/bis-isobutyl PPG-20 Crosspolymer (trade name Dow Corning® DC EL 8051 IN), mixtures with the INCI name Dimethicone/Vinyl Dimethicone Crosspolymer (and) C12-14 Pareth-12) (trade name Dow Corning® DC 9509), and mixtures with the INCI name Dimethicone/Vinyl Dimethicone Crosspolymer (and) Silica (trade name Dow Corning® DC 9701 Cosmetic Powder).

Suitable polymers are likewise polysaccharides, in particular xanthan gum, guar gum, agar agar, alginates and tyloses, and also tara gum, carrageenan, sclerotium gum and natural cellulose.

Further Oil Bodies b-4)

Bodycare compositions such as creams, body oils, lotions and milks, usually comprise a series of further oil bodies and emollients which contribute to further optimizing the sensory properties. The oil bodies (esters according to the invention plus further oil bodies) are present usually in a total amount of 0.1-80, in particular 0.5 to 70, 1 to 60, 1 to 50% by weight, 1 to 40% by weight, 5-25% by weight or 5-15% by weight. The further oil bodies are usually present in an amount of from 0.1 to 40% by weight.

Suitable further oil bodies are, for example, Guerbet alcohols based on fatty alcohols having 6 to 18, for example 8 to 10, carbon atoms, and also further additional esters such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of $C_{18}$-$C_{38}$-alkylhydroxycarboxylic acids with linear or branched $C_6$-$C_{22}$-fatty alcohols, in particular dioctyl malate, esters of linear and/or branched fatty acids with polyhydric alcohols (such as e.g. propylene glycol, dimerdiol or trimertriol), triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as e.g. Dicaprylyl Carbonate (Cetiol® CC), Guerbet carbonates based on fatty alcohols having 6 to 18, for example 8 to 10 carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as e.g. Dicaprylyl ether (Cetiol® OE), ring-opening products of epoxidized fatty acid esters with polyols and hydrocarbons or mixtures thereof. Also suitable are esters of 2-propylheptanol with n-octanoic acid, as e.g. commercially available under the trade name Cetiol® SenSoft (Cognis GmbH). Also suitable are hydrocarbons, such as, for example, undecane and tridecane. Also suitable are alkanes, such as e.g. the mixtures with the INCI name Coconut/Palm/Palm Kernel Oil Alkanes (trade name Vegelight 1214 from Biosynthesis).

Surprisingly, it has been found that the esters according to the invention are suitable in particular for solubilizing oil-soluble UV photoprotective filters.

The invention provides preparations comprising at least one ester as described herein and at least one UV photoprotective filter, such as an oil-soluble UV photoprotective filter.

The invention provides preparations comprising at least one ester selected from the group consisting of n-nonyl n-octanoate, n-nonyl n-nonanoate, n-nonyl n-decanoate, n-decyl n-octanoate, n-decyl n-nonanoate, n-decyl n-decanoate, n-octyl n-nonanoate, n-octyl n-decanoate, n-heptyl n-octanoate, n-heptyl n-nonanoate, n-heptyl n-decanoate, n-nonyl isooctanoate (in particular n-nonyl 2-ethylhexanoate), isononyl n-octanoate (in particular 3,5,5-trimethylhexyl n-octanoate), n-nonyl isononanoate, (in particular n-nonyl 3,5,5-trimethylhexanoate), isononyl n-nonanoate (in particular 3,5,5-trimethylhexyl n-nonanoate), n-octyl isononanoate (in particular n-octyl 3,5,5-trimethylhexanoate), isooctyl n-nonanoate (in particular 2-ethylhexyl n-nonanoate), n-octyl isooctanoate (in particular n-octyl 2-ethylhexanoate), n-decyl isooctanoate (in particular n-decyl 2-ethylhexanoate), n-decyl isononanoate (in particular n-decyl 3,5,5-trimethylhexanoate), isononyl n-decanoate (in particular 3,5,5-trimethylhexyl n-decanoate), n-heptyl n-dodecanoate, isononyl isooctanoate (in particular 3,5,5-trimethylhexyl 2-ethylhexanoate), and at least one UV photoprotective filter, for example an oil-soluble UV photoprotective filter.

According to the invention, suitable UV photoprotective filters are organic substances (photoprotective filters) that are liquid or crystalline at room temperature and which are able to absorb ultraviolet rays and release the absorbed energy again in the form of longer-wave radiation, e.g. heat. UV filters can be oil-soluble or water-soluble. Typical oil-soluble UV-B filters or broad spectrum-UV A/B filters to be mentioned are e.g.:

3-benzylidenecamphor or 3-benzylidenenorcamphor (Mexoryl SDS 20) and derivatives thereof, e.g. 3-(4-methylbenzylidene)camphor, as described in EP 0693471 B1

3-(4'-trimethylammonium)benzylidenebornan-2-one methylsulfate (Mexoryl SO)

3,3'-(1,4-phenylenedimethine)bis(7,7-dimethyl-2-oxobicyclo[2.2.1]heptane-1-methanesulfonic acid) and salts (Mexoryl SX)

3-(4'-sulfo)benzylidenebornan-2-one and salts (Mexoryl SL)

polymer of N-{(2 and 4)-[2-oxoborn-3-ylidene)-methyl}benzyl]acrylamide (Mexoryl SW)

2-(2H-benzotriazol-2-yl)-4-methyl-6-(2-methyl-3-(1,3,3,3-tetramethyl-1-(trimethylsilyloxy)disiloxanyl)propyl)phenol (Mexoryl SL)

4-aminobenzoic acid derivatives, for example 2-ethylhexyl 4-(dimethylamino)benzoate, 2-octyl 4-(dimethylamino) benzoate and amyl 4-(dimethylamino)benzoate;

esters of cinnamic acid, for example 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);

esters of salicylic acid, for example 2-ethylhexyl salicylate, 4-isopropylbenzyl salicylate, homomenthyl salicylate;

derivatives of benzophenone, for example 2-hydroxy-4-methoxybenzophenone, 2-hydroxy-4-methoxy-4'-methylbenzophenone, 2,2'-dihydroxy-4-methoxybenzophenone;

esters of benzalmalonic acid, for example di-2-ethylhexyl 4-methoxybenzmalonate;

triazine derivatives, such as e.g. 2,4,6-trianilino(p-carbo-2'-ethyl-1'-hexyloxy)-1,3,5-triazine and 2,4,6-tris[p-(2-ethylhexyloxycarbonyl)anilino]-1,3,5-triazine (Uvinul T 150) as described in EP 0818450 A1 or bis(2-ethylhexyl) 4,4'-[(6-[4-((1,1-dimethylethyl)aminocarbonyl)phenylamino]-1,3,5-triazine-2,4-diyl)diimino]bisbenzoate (Uvasorb® HEB);

2,2-(methylenebis(6-(2H-benzotriazol-2-yl)-4-(1,1,3,3-tetramethylbutyl)phenol) (Tinosorb M);
2,4-bis[4-(2-ethylhexyloxy)-2-hydroxyphenyl]-6-(4-methoxyphenyl)-1,3,5-triazine (Tinosorb S);
Propane-1,3-diones, such as e.g. 1-(4-tert-butylphenyl)-3-(4'-methoxyphenyl)propane-1,3-dione;
Ketotricyclo(5.2.1.0)decane derivatives, as described in EP 0694521 B1;
Dimethicodiethylbenzalmalonates (Parsol SLX).
Suitable water-soluble UV filters are:
2-phenylbenzimidazole-5-sulfonic acid and the alkali metal, alkaline earth metal, ammonium, alkyl ammonium, alkanol ammonium and glucammonium salts thereof;
2,2-((1,4-phenylene)bis(1H-benzimidazole-4,6-disulfonic acid, monosodium salt) (Neo Heliopan AP)
sulfonic acid derivatives of benzophenones, for example 2-hydroxy-4-methoxybenzophenone-5-sulfonic acid and its salts;
sulfonic acid derivatives of 3-benzylidenecamphor, such as e.g. 4-(2-oxo-3-bornylidenemethyl)benzenesulfonic acid and 2-methyl-5-(2-oxo-3-bornylidene)sulfonic acid and salts thereof.

In one or more embodiments of the invention, the preparations comprise at least one oil-soluble UV photoprotective filter and at least one water-soluble UV photoprotective filter. Suitable typical UV-A filters are in particular derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol® 1789), 1-phenyl-3-(4'-isopropylphenyl)propane-1,3-dione, and also enamine compounds, as described in DE 19712033 A1 (BASF), and also benzoic acid, 2-[4-(diethylamino)-2-hydroxybenzoyl]-, Hexyl Ester (Uvinul® A plus).

The UV-A and UV-B filters can of course also be used in mixtures. Particularly favorable combinations consist of the derivatives of benzoylmethane, e.g. 4-tert-butyl-4'-methoxydibenzoylmethane (Parsol® 1789) and 2-ethylhexyl 2-cyano-3,3-phenylcinnamate (octocrylene) in combination with esters of cinnamic acid, such as 2-ethylhexyl 4-methoxycinnamate and/or propyl 4-methoxycinnamate and/or isoamyl 4-methoxycinnamate. Combinations of this type are advantageously combined with water-soluble filters such as e.g. 2-phenylbenzimidazole-5-sulfonic acid and the alkali metal, alkaline earth metal, ammonium, alkyl ammonium, alkanol ammonium and glucammonium salts thereof.

Suitable UV photoprotective filters are in particular the substances approved according to annex VII of the Commission Directive (in the version Commission Directive 2005/9/EC of 28 Jan. 2005 amending Council Directive 76/768/EEC, concerning cosmetic products, for the purposes of adapting Annexes VII thereof to technical progress), to which reference is explicitly made here.

The preparations according to the invention can also comprise insoluble photoprotective pigments, namely finely disperse metal oxides and/or salts. Examples of suitable metal oxides are in particular zinc oxide and titanium dioxide and also oxides of iron, zirconium, silicon, manganese, aluminum and cerium, and mixtures thereof. Salts which can be used are silicates (talc), barium sulfate or zinc stearate. The oxides and salts are used in the form of the pigments for skincare and skin-protecting emulsions and also for decorative cosmetics. The particles should have an average diameter of less than 100 nm, for example between 5 and 50 nm or between 15 and 30 nm. They can have a spherical form, although it is also possible to use particles which have an ellipsoidal form or a form which deviates in some other way from the spherical shape. The pigments can also be present in surface-treated form, i.e. hydrophilicized or hydrophobicized. Typical examples thereof are coated titanium dioxides, such as e.g. titanium dioxide T 805 (Degussa) or Eusolex® T, Eusolex® T-2000, Eusolex® T-Aqua, Eusolex® AVO, Eusolex® T-ECO, Eusolex® T-OLEO and Eusolex® T-S (Merck). Typical examples thereof are zinc oxides, such as e.g. zinc oxide neutral, zinc oxide NDM (Symrise) or Z-Cote® (BASF) or SUNZnO-AS and SUNZnO-NAS (Sunjun Chemical Co. Ltd.). Suitable hydrophobic coatings here are primarily silicones and specifically trialkoxyoctylsilanes or simethicones. In sunscreen compositions, so-called micropigments or nanopigments are typically used. In certain embodiments micronized zinc oxide is used. Further suitable UV photoprotective filters can be found in the overview by P. Finkel in SÖFW Journal 122, August 1996, pp. 543-548, and Parf. Kosm. Volume 80, No. March 1999, pp. 10 to 16.

As well as the two aforementioned groups of primary photoprotective substances, it is also possible to use secondary photoprotective agents of the antioxidant type, which interrupt the photochemical reaction chain which is triggered when UV radiation penetrates into the skin. Typical examples thereof are amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. -carotene, -carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, linoleyl, cholesteryl and glyceryl esters thereof), and salts thereof, dilauryl thiodipropionate, distearyl thiodipropionate, thiodipropionic acid and derivatives thereof (esters, ethers, peptides, lipids, nucleotides, nucleosides and salts), and also sulfoximine compounds (e.g. buthionine sulfoximines, homocysteine sulfoximine, buthionine sulfones, penta-, hexa-, heptathionine sulfoximine) in very low tolerated doses (e.g. pmol to mol/kg), also (metal) chelating agents (e.g. α-hydroxy fatty acids, palmitic acid, phytic acid, lactoferrin), α-hydroxy acids (e.g. citric acid, lactic acid, maleic acid), humic acid, bile acid, bile extracts, bilirubin, biliverdin, EDTA, EGTA and derivatives thereof, unsaturated fatty acids and derivatives thereof (e.g. gamma-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, ZnSO4), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) suitable according to the invention of these specified active ingredients.

In one or more embodiments of the invention, the preparations comprise at least one UV photoprotective filter selected from the group consisting of 4-methylbenzylidenecamphor, benzophenone-3, butylmethoxydibenzoyl methane, bis-ethylhexyloxyphenol methoxyphenyl triazine, methylene bis-benzotriazolyl tetramethylbutylphenol, diethylhexyl butamidotriazone, ethylhexyl triazone and diethylamino hydroxybenzoyl hexyl benzoate, 3-(4'-trimethylammonium)benzylidenebornan-2-one methylsulfate, 3,3'-(1,4-phenylenedimethine)bis(7,7-dimethyl-2-oxobicyclo[2.2.1]heptane-1-methanesulfonic acid) and its salts, 3-(4'sulfo)benzylidenebornan-2-one and its salts, polymer of N-{(2 and 4)-[2-oxoborn-3-ylidene)methyl}benzyl]acrylamide, 2-(2H-benzotriazol-2-yl)-4-methyl-6-(2-methyl-3-(1, 3,3,3-tetramethyl-1-(trimethylsilyloxy)disiloxanyl)propyl) phenol, dimethicodiethyl benzalmalonate and their mixtures.

These UV photoprotective filters are commercially available, for example, under the following trade names:

NeoHeliopan® MBC (INCI: 4-methylbenzylidene camphor; manufacturer: Symrise); NeoHeliopan® BB (INCI: benzophenone-3, manufacturer: Symrise); Parsol® 1789 (INCI: butyl methoxydibenzoylmethane, manufacturer: Hoffmann La Roche (Givaudan); Tinosorb® S (INCI: bis-ethylhexyloxyphenol methoxyphenyl triazine); Tinosorb® M (INCI: methylene bis-benzotriazolyl tetramethylbutylphenol): manufacturer: Ciba Specialty Chemicals Corporation; Uvasorb® HEB (INCI: diethylhexyl butamidotriazone, manufacturer: 3V Inc.), Unvinul®T 150 (INCI: ethylhexyl triazone, manufacturer: BASF AG); Uvinul® A plus (INCI: diethylamino hydroxybenzoyl hexyl benzoate: manufacturer: BASF AG; Mexoryl® SO: 3-(4'-trimethylammonium)-benzylidenebornan-2-one methylsulfate, INCI: camphor benzalkonium methosulfate; Mexoryl® SX: 3,3'-(1,4-phenylenedimethine)bis(7,7-dimethyl-2-oxobicyclo[2.2.1]heptane-1-methanesulfonic acid), CTFA: INCI terephthalylidene dicamphor sulfonic acid; Mexory® SL: 3-(4'-sulfo)benzylidenebornan-2-one, INCI benzylidene camphor sulfonic acid; Mexoryl® SW: polymer of N-{(2 and 4)-[2-oxoborn-3-ylidene)methyl}benzyl]acrylamide, INCI polyacrylamidomethyl benzylidene camphor; Mexoryl® SL: 2-(2H-benzotriazol-2-yl)-4-methyl-6-(2-methyl-3-(1,3,3,3-tetramethyl-1-(trimethylsilyloxy)disiloxanyl)propyl)phenol; INCI: DROMETRIZOLE TRISILOXANE; Parsol® SLX: dimethicodiethylbenzalmalonate, INCI polysilicone-15.

The preparations according to the invention can comprise the UV photoprotective filters in amounts of from 0.5 to 30% by weight, 2.5 to 20% by weight, or 5-15% by weight—based on the preparation.

Further Ingredients

Suitable thickeners are, for example, Aerosil grades (hydrophilic silicas), carboxymethylcellulose and hydroxyethyl- and hydroxypropylcellulose, polyvinyl alcohol, polyvinylpyrrolidone and bentonite such as e.g. Bentone® Gel VS-5PC (Rheox). A suitable thickener is for example the product with the INCI name Dicaprylyl Carbonate, Stearalkonium Hectorite and Propylene Carbonate available under the trade names Cosmedia® Gel CC. Biogenic active ingredients are to be understood as meaning, for example, tocopherol, tocopherol acetate, tocopherol palmitate, ascorbic acid, (deoxy)ribonucleic acid and a fragmentation product thereof, β-glucans, retinol, bisabolol, allantoin, phytantriol, panthenol, AHA acids, amino acids, ceramides, pseudoceramides, essential oils, plant extracts, such as e.g. prune extract, bambara nut extract and vitamin complexes. Deodorizing active ingredients/antiperspirants counteract, mask or eliminate body odors. Body odors are formed as a result of the action of skin bacteria on apocrine perspiration, during which unpleasant smelling degradation products are formed. Accordingly, antimicrobial agents, enzyme inhibitors, odor absorbers or odor maskers, inter alia, are suitable as deodorizing active ingredients. Suitable insect repellents are, for example, N,N-diethyl-m-toluamide, 1,2-pentanediol or ethyl 3-(N-n-butyl-N-acetylamino)propionate), which is sold under the name Insect Repellent® 3535 by Merck KGaA, and also butylacetylaminopropionate. A suitable self-tanning agent is dihydroxyacetone or erythrulose. Suitable tyrosine inhibitors, which prevent the formation of melanin and are used in depigmentation compositions, are, for example, arbutin, ferulic acid, kojic acid, cumaric acid and ascorbic acid (vitamin C). Suitable preservatives are, for example, phenoxyethanol, formaldehyde solutions, parabens, pentanediol, chlorphenesin, caprylyl glycol, ethylhexylglycerols or sorbic acid, and also the silver complexes known under the name Surfacine® and the other substance classes listed in annex 6, part A and B of the Cosmetics Ordinance. Perfume oils which may be mentioned are mixtures of natural and synthetic fragrances. Natural fragrances are extracts from flowers, stems and leaves, fruits, fruit peels, roots, woods, herbs and grasses, needles and branches, resins and balsams. Also suitable are animal raw materials, such as, for example, civet and castoreum, and also synthetic fragrance compounds of the ester, ether, aldehyde, ketone, alcohol and hydrocarbon types. Suitable pearlescent waxes or pearlescent compounds, particularly for use in surface-active formulations, are, for example: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have in total at least 24 carbon atoms, specifically laurone and distearyl ether; stearyl citrate, cyclodextrin, fatty acids such as stearic acid, hydroxystearic acid or behenic acid, ring-opening products of olefin epoxides having 12 to carbon atoms with fatty alcohols having 12 to 22 carbon atoms and/or polyols having 2 to 15 carbon atoms and 2 to 10 hydroxyl groups, and mixtures thereof. Superfatting agents which can be used are substances such as, for example, lanolin and lecithin, and also polyethoxylated or acylated lanolin and lecithin derivatives, polyol fatty acid esters, monoglycerides and fatty acid alkanolamides, the latter simultaneously serving as foam stabilizers. A suitable superfatting agent is, for example, the mixture of cocoglucosides and glyceryl oleate (commercially available as Lamesoft® PO65 from Cognis GmbH).

Suitable fillers are substances which, for example, improve the sensory or cosmetic properties of a preparation and which, for example, produce or boost a velvety or silky feel (so-called skin sensory modifier). Suitable fillers are starch and starch derivatives (such as e.g. tapioca starch, aluminum starch octenyl succinate, sodium octenyl succinate, distarch phosphate), pigments which do not serve primarily as UV filters or dyes (such as e.g. boron nitride) and/or Aerosil® (CAS No. 7631-86-9), and/or talc, and also for example polymethyl methacrylate (e.g. Cosmedia® PMMA V8/V12), silica (e.g. Cosmedia® SILC), stearalkonium hectorite (as present in the commercially available product Cosmedia® gel CC), and also HDI/trimethylol hexyllactone crosspolymer (as present in the commercially available product Cosmedia® CUSHION).

Stabilizers which can be used are metal salts of fatty acids, such as e.g. magnesium, aluminum and/or zinc stearate or ricinoleate. To improve the flow behavior, also hydrotropes, such as, for example, ethanol isopropyl alcohol, or polyols, can be used. Polyols which are suitable here have for example 2 to 15 carbon atoms and at least two hydroxyl groups. The polyols can also contain further functional groups, in particular amino groups, and/or be modified with nitrogen.

The preparations according to the invention, and also the esters according to the invention are suitable in particular in cosmetic and/or pharmaceutical preparations for the wetting or impregnation or coating of utility wipes and hygiene wipes which are used for cleaning the body and/or for bodycare.

Utility wipes and hygiene wipes which may be mentioned by way of example are: tissues, papers, wipes, nonwoven products, sponges, puffs, plasters and bandages which are used in the field of hygiene and care. These may be wet wipes for baby hygiene and babycare, cleansing wipes, face cleansing wipes, skincare wipes, care wipes with active ingredients to combat skin aging, wipes with sunscreen formulations and insect repellents, and also wipes for decorative cosmetics or for after-sun treatment, toilet wet wipes, antiperspirant wipes, diapers, pocket tissues, wet wipes, hygiene products, and self-tanning wipes.

EXAMPLES

Example 1

Preparation of N-Decyl-N-Decanoic Acid 1 mol of n-decanol and 1 mol of n-decanoic acid and also 0.22 g 0.22 g of Fascat® 2001 (Sn oxalate) are heated at a temperature of 240° C. for 3 hours on a water separator. The product is distilled over a 30 cm column (153-168° C. at 0.8 mbar). The product is a colorless, odorless oil.

FORMULATION EXAMPLES

The formulations specified below are obtained by adding the ester as in preparation example 1 to the formulations. In an analogous manner, cosmetic formulations are obtained in which the following esters are used:

n-nonyl n-octanoate, n-nonyl n-nonanoate, n-nonyl n-decanoate, n-decyl n-octanoate, n-decyl n-nonanoate, n-decyl n-decanoate, n-octyl n-nonanoate, n-octyl n-decanoate, n-heptyl n-octanoate, n-heptyl n-nonanoate, n-heptyl n-decanoate, n-nonyl isooctanoate (in particular n-nonyl 2-ethylhexanoate), isononyl n-octanoate (in particular 3,5,5-trimethylhexyl n-octanoate), n-nonyl isononanoate (in particular n-nonyl 3,5,5-trimethylhexanoate), isononyl n-nonanoate (in particular 3,5,5-trimethylhexyl n-nonanoate), n-octyl isononanoate (in particular n-octyl 3,5,5-trimethylhexanoate), isooctyl n-nonanoate (in particular 2-ethylhexyl n-nonanoate), n-octyl isooctanoate (in particular n-octyl 2-ethylhexanoate), n-decyl isooctanoate (in particular n-decyl 2-ethylhexanoate), n-decyl isononanoate (in particular n-decyl 3,5,5-trimethylhexanoate), isononyl n-decanoate (in particular 3,5,5-trimethylhexyl n-decanoate), n-heptyl n-dodecanoate, isononyl isooctanoate (in particular 3,5,5-trimethylhexyl 2-ethylhexanoate).

TABLE 1

O/W bodycare emulsions

| Ingredients<br>C—cream, L—lotion | 1<br>C | 2<br>C | 3<br>C | 4<br>L | 5<br>C | 6<br>L | 7<br>L | 8<br>C | 9<br>L | 10<br>C | 11<br>C |
|---|---|---|---|---|---|---|---|---|---|---|---|
| Eumulgin ® VL 75 | | | | | | | | 2.0 | | 1.5 | |
| Dehymuls ® PGPH | | 0.6 | | | | | | | | | |
| Generol ® R | | | 0.5 | | | | | | | | |
| Eumulgin ® B2 | | | 2.0 | | | | | | 2.0 | | |
| Tween ® 60 | | | | 0.2 | | | | | | | |
| Cutina ® E 24 | | | | 0.2 | | | | | | | |
| Hostaphat ® KL 340 N | | | | | | | | | | 0.5 | |
| Lanette ® E | | | | | | | | | 0.6 | | |
| Amphisol ® K | | | | 0.2 | | | | | | | |
| Sodium Stearate | | | | | 0.5 | | | | | | |
| Emulgade ® PL 68/50 | 3.0 | | | | | | 2.0 | | | | 1.2 |
| Eumulgin ® SG | 0.2 | | | | 0.2 | 0.3 | | | | | |
| Eumulgin ® Prisma | | 0.2 | | | | | 0.2 | | | 0.2 | 0.5 |
| Inwitor 372 P | | | | | | 3.0 | | | | 3.0 | |
| Tego ® Care CG | 0.7 | | | | | | | | | | |
| Tego ® Care 450 | | | | | 3 | | 1.0 | | | 1.0 | |
| Cutina ® PES | 2.5 | 2 | 3 | | | 2 | | 1.7 | 2.5 | | 1.2 |
| Cutina ® MD | | 1 | | 3 | 5 | | 2 | | | 3 | |
| Lanette ® 14 | | | | 1 | | | | 4 | | | 4 |
| Lanette ® O | 4.5 | | 4 | | 1 | | | | | | 2 |
| Novata ® AB | | 1 | | | | | | | | | 1 |
| Emery ® 1780 | | | | | 0.5 | 0.5 | | | | | |
| Lanolin, water-free, USP | | | | | | | 1.1 | | | | |
| Cosmedia ® DC | | 1.5 | 2 | | | 1.5 | 2 | | 1.5 | 1.5 | |
| Cetiol ® SB 45 | | | 1.5 | | | | 2 | | | | |
| Cegesoft ® C 17 | | | | | | | | | | | 2 |
| Myritol ® PC | | | | 5 | | | | | | | |
| Myritol ® 331 | 2 | 5 | 1 | | | 6 | | 6 | | | |
| Finsolv ® TN | | | 2 | | | 2 | | | | | |
| Ester as in Example 1 | 4 | 3 | 4 | 5 | 4 | 4 | 4 | 6 | 8 | 3 | 5 |
| Cetiol ® Sensoft | 2.0 | | | | | 2.0 | | | | 3.0 | |
| Cetiol ® CC | | | 3 | | | | 4 | | | | 5 |
| Cetiol ® OE | | | | 2.0 | | | | | 4 | | |
| Dow Corning DC ® 245 | | | | 2 | | 1 | 1 | | | | |
| Dow Corning DC ® 2502 | | | | | | 2 | 1 | | | | |
| Prisorine ® 3758 | | | | | | | 1 | | | | |
| Silicone Oil Wacker AK ® 350 | 0.5 | 0.5 | 0.5 | | | | 1 | | | | |
| Cetiol ® 868 | | | | | | 2 | 4 | | | | |
| Cetiol ® J 600 | 2 | | 3 | | 3 | 2 | | | | 5 | |
| Ceraphyl ® 45 | | | | | | | | 3 | | | |
| Mineral Oil | | | | | 9 | | | | | | |
| Cetiol ® SN | | | | 5 | | | | | | | |
| Cetiol ® B | | | | | | | | | 4 | | 2 |
| Eutanol ® G | | 2 | | 3 | | | | | | | |
| Cetiol ® PGL | | | | | | | | | 5 | 5 | |
| Dry Flo ® Plus | 5 | | | | | | 1 | | | | |
| SFE 839 | | 5 | | | | | | | | | 2 |

TABLE 1-continued

O/W bodycare emulsions

| Ingredients | 1 | 2 | 3 | 4 | 5 | 6 | 7 | 8 | 9 | 10 | 11 |
|---|---|---|---|---|---|---|---|---|---|---|---|
| C—cream, L—lotion | C | C | C | L | C | L | L | C | L | C | C |
| Almond Oil | | | | | | | 1 | | | | |
| Insect Repellent ® 3535 | | 2 | 4 | | | 2 | | | | 3 | |
| N,N-Diethyl-m-toluamide | | 2 | | | | | | | | 3 | |
| Photonyl ® LS | 2 | 2 | | | | 2 | | | | | |
| Panthenol | | | | | | | 1 | | | | |
| Bisabolol | | | | | | | 0.2 | | | | |
| Tocopherol/Tocopheryl Acetate | | | | | | | 1 | | | | |
| Veegum ® Ultra | | | | | | | | 1 | | | |
| Keltrol ® T | | | 0.4 | | | | | 0.5 | | | |
| Cosmedia ® SP | | 0.3 | | 0.2 | 0.2 | | | 0.2 | 0.3 | | |
| Pemulen ® TR 2 | 0.3 | | | | | | 0.3 | | | | |
| Carbopol ® Ultrez 10 | | | | | 0.2 | | | | | | |
| Rheocare ® C Plus | | | 0.3 | 0.2 | | | | | | | |
| Ultragel ™ 300 | | | | | | | | 0.2 | | | |
| Ethanol | | | | | | | | | | 10 | |
| Butylene glycol | | | | 4 | 3 | | 2 | 5 | 2 | | |
| Glycerin | 2 | 5 | 5 | | 3 | 3 | 2 | 4 | | | 3 |
| Water, Preservatives, NaOH | ad 100, q.s., pH 6.5-7.5 | | | | | | | | | | |

TABLE 2

O/W bodycare emulsions

| Ingredients | 12 | 13 | 14 | 15 | 16 | 17 | 18 | 19 | 20 | 21 | 22 |
|---|---|---|---|---|---|---|---|---|---|---|---|
| C—cream, L—lotion | C | C | L | C | L | C | C | L | L | L | C |
| Eumulgin ® VL 75 | | | 1 | | | | | | | 1 | |
| Generol ® R | | | | 0.3 | | | | | | | |
| Eumulgin ® B2 | | | | | | | | 2 | | | |
| Tween ® 60 | | | 2 | | | | | 1 | | | |
| Cutina ® E 24 | | | 0.5 | | | | | 1 | | | |
| Lanette ® E | 0.5 | | | | | | | | | | |
| Amphisol ® K | | 0.5 | | | | | | 0.1 | | | |
| Sodium Stearate | | | | 1 | | | | | | | |
| Emulgade ® PL 68/50 | | 3 | | | | 3.0 | 1 | 2 | | | |
| Eumulgin ® SG | | | | | | 0.5 | | | | | 0.5 |
| Eumulgin ® Prisma | | 0.5 | | | 0.2 | 0.2 | | | | | |
| Inwitor 372 P | 3 | 2 | 3 | | 3 | | 1 | 1 | | | |
| Tego ® Care 450 | | | | 1 | | 2.0 | 3.8 | 1 | 1 | | |
| Cutina ® PES | 2 | | 1 | 2.5 | 2 | | 1.2 | | 1.5 | 3 | |
| Cutina ® MD | 3 | 1 | | 4 | | | | | | | |
| Lanette ® 14 | | 2 | | 1 | | | 2 | | 1 | | |
| Lanette ® O | 2 | | 2 | | 3 | 1 | | 1 | 1 | 6 | |
| Novata ® AB | | | | | | | | | 1 | 1 | |
| Emery ® 1780 | | | | | | | | | | | 0.5 |
| Lanolin, water-free, USP | | | | 4 | | | | | | | |
| Cosmedia ® DC | | 1 | | | 1.5 | | 1 | 1 | | | |
| Cetiol ® SB 45 | | | | | 2 | | | | | | |
| Cegesoft ® C 17 | | 4 | | | | | | | | | |
| Myritol ® PC | 6 | | | | 5 | | 5 | | | | |
| Myritol ® 331 | | 5 | | | 7 | | | 10 | | 3 | |
| Finsolv ® TN | | 5 | | 4 | 5 | | | | | 1 | |
| Ester as in Example 1 | 5 | 2 | 4 | 6 | 2 | 5 | 4 | 3 | 3 | 8 | 2 |
| Cetiol ® Sensoft | | 2 | 3 | | | | | | | | |
| Cetiol ® CC | | | 4 | | | | 3 | | | | |
| Cetiol ® OE | 2.5 | | | | | 2 | 5 | | | | 2 |
| Dow Corning DC 245 | | 1 | | | 1 | | | | | | 3 |
| Dow Corning DC 2502 | 3 | | | | | | | | | | 2 |
| Prisorine ® 3758 | | | | | | | | | | | |
| Silicone Oil Wacker AK 350 | | | | | | 1 | | | | | 1 |
| Cetiol ® 868 | | 2 | | | | | | | | | |
| Cetiol ® J 600 | | 2 | | | 2 | | | | | | |
| Ceraphyl ® 45 | | | | | | | | 3 | | | |
| Cetiol ® SN | | | | 5 | | | | | | | |
| Cetiol ® B | | | | | 5 | | 4 | | | | 3 |
| Eutanol ® G | | | 3 | | 5 | | | | | | |
| Cetiol ® PGL | | | | | | | | | 5 | 2 | |
| Dry Flo ® Plus | | | 1 | | | | | | | | 1 |
| SFE 839 | 1 | 1 | | | | | | | | | |
| Almond Oil | | | | | 2 | | | | | | |
| Photonyl ® LS | | | | | 2 | | | | | | |
| Panthenol | | | | | | 1 | | | | | |
| Bisabolol | | | | | | 0.2 | | | | | |
| Tocopherol/Tocopheryl Acetate | | | | | | 1 | | | | | |
| Veegum ® Ultra | | | | | | | | | | 1 | |
| Keltrol ® T | | | | | | | | | 0.5 | | |
| Cosmedia ® SP | 0.1 | | 1 | | 0.2 | 0.2 | 0.2 | 0.2 | | | 0.5 |
| Carbopol ® ETD 2001 | | | | 0.3 | | | | | | | |
| Pemulen ® TR 2 | | | | | | | 0.3 | | | | |
| Rheocare ® C Plus | 0.2 | 0.3 | | | | | | | | | |
| Ultragel ™ 300 | | | | | 0.4 | 0.3 | | | 0.4 | | |
| Ethanol | | | 5 | | 8 | | | | | | 10 |
| Butylene glycol | 5 | | | 3 | 3 | | | | | 8 | |
| Glycerin | 2 | 4 | 3 | 3 | | | 7 | 5 | 3 | 5 | |
| Water, Preservatives, NaOH | ad 100, q.s., (pH 6.5-7.5) | | | | | | | | | | |

TABLE 3

O/W body care emulsions

| Ingredients C—Cream, L—Lotion, SC = Sprayable Cream | 23 SC | 24 C | 25 C | 26 L | 27 C |
|---|---|---|---|---|---|
| Dehyquart ® C 4046 | 6 | | | 3 | |
| Cutina ® GMS-SE | | | | | 5.5 |
| Cutina ® FS 45 | | | | | 1.5 |
| Eumulgin ® B2 | | 1 | | | |
| Eumulgin ® SG | | | 0.2 | | |
| Eumulgin ® Prisma | | 0.2 | | | |
| Inwitor 372 P | | | 2 | | |
| Cutina ® PES | 3 | 2 | 2 | 2 | 2 |
| Cutina ® MD | | 1.5 | | | |
| Cosmedia ® DC | | | | 0.5 | |
| Cegesoft ® PS 6 | | | | 4.5 | |
| Cegesoft ® SH | | 7 | 3 | | |
| Myritol ® 331 | | | 5 | 4.5 | |
| Ester as in Example 1 | 4 | 5 | 4 | 3 | 4 |
| Cetiol ® Sensoft | | 2 | | | |
| Cetiol ® CC | | | 3 | | |
| Cetiol ® OE | | 1 | | | |
| Silicone Oil Wacker AK ® 350 | | | | 0.5 | |
| Paraffin Liquid | | | | | 2 |
| Isopropyl Palmitate | | | 2 | | |
| Cetiol ® 868 | | 2 | 4 | | |
| Cetiol ® SN | 4 | | | | 3 |
| Eutanol ® G | | | | | 3 |
| Almond Oil | | 7 | | | |
| Panthenol | 1 | 0.2 | 1 | | |
| Bisabolol | | | | 1 | |
| Tocopherol/Tocopheryl Acetate | | | | 0.2 | |
| Keltrol ® T | | | | 1 | |
| Ultragel ™ 300 | 0.1 | | | 0.45 | |
| Cosmedia ® SP | | 1 | 0.7 | | |
| Glycerin | 2 | 5 | 5 | 5 | |
| Water, Preservatives, NaOH | ad 100, q.s. | | | | |

TABLE 4

W/O bodycare emulsions

| Ingredients (INCI) C—cream, L—lotion | 1 C | 2 L | 3 C | 4 L | 5 C | 6 L | 7 L | 8 L | 9 C | 10 C | 11 C |
|---|---|---|---|---|---|---|---|---|---|---|---|
| Dehymuls ® PGPH | 1 | 2 | 1 | 2 | 3 | 1 | 1 | 2 | | | 1 |
| Monomuls ® 90-O18 | 2 | | | | | | | 2 | | | 2 |
| Lameform ® TGI | 4 | 1 | | | 3 | | 1 | 4 | 3 | | |
| Abil ® EM 90 | | | | | | 4 | | 1 | | | |
| Isolan GPS | | | 2 | | 2 | | | | 1 | | |
| Isolane ® PDI | | | | | | 4 | | | | 1 | |
| Glucate ® DO | | | | 3 | | | | | | | |
| Arlacel ® 83 | | | 4 | | | | | | | | |
| Dehymuls ® LE | | 1 | 1 | 2 | | | | | 1 | 1 | |
| Dehymuls ® HRE 7 | | | | | | 4 | 1 | | | | |
| Zinc Stearate | 2 | 1 | | 1 | 1 | | | 1 | 1 | 1 | |
| Microcristalline Wax | | 5 | | | 2 | | | | | | 5 |
| Bees wax | 4 | | 1 | | | 1 | | 1 | 4 | 7 | |
| Tego Care ® CG | | | | | 1 | | | | | | 0.5 |
| Prisorine ® 3505 | | | 1 | 1 | | 1 | 1 | | | | 1 |
| SFE ® 839 | | | | | | | 3 | | | | |
| Emery ® 1780 | 1 | | | | | | | | | | 1 |
| Anhydrous Lanolin USP | | 5 | | | | | | | | 4 | |
| Ester as in Example 1 | 3 | 4 | 2 | 6 | 6 | 2 | 2 | 6 | 3 | 8 | 1 |
| Cegesoft ® C 17 | | | 3 | | | | | | 1 | | |
| Myritol ® PC | | | | | 2 | 4 | | | | | |
| Myritol ® 331 | 6 | | | | 2 | 6 | 2 | | | | 8 |
| Finsolv ® TN | | | | 5 | | 2 | 5 | | | | |
| Cetiol ® A | | | 6 | | | 4 | | | | | |
| Cetiol ® Sensoft | | | | 6 | 4 | | | | | 4 | |
| Cetiol ® CC | | 8 | | | 2 | 2 | 2 | | | | 5 |
| Cetiol ® SN | | 5 | | | | | 3 | | | | |
| Cetiol ® OE | 3 | | | 4 | | 2 | | 4 | 2 | | |
| Dow Corning DC ® 244 | | | | 1 | | 2 | | | | | |
| Dow Corning DC ® 2502 | | 1 | | 2 | | | | | | | |
| Prisorine ® 3758 | | | | | 3 | | | | | | |
| Silicone Oil Wacker AK ® 350 | | | | 4 | | | 3 | | | | |
| Cetiol ® 868 | | | | | | | | | | 2 | 7 |
| Cetiol ® J 600 | | 4 | | | 2 | | | | | | |
| Ceraphyl ® 45 | | | 2 | | | 2 | | | | 6 | |
| Mineral oil | | | 4 | | | | | | | | |
| Cetiol ® B | | 2 | 4 | | | | | | 3 | | |
| Eutanol ® G 16 | 1 | | | | | | | | | 3 | |
| Eutanol ® G | | 3 | | | | | | 8 | | | |
| Cetiol ® PGL | | | | 4 | | | | 9 | | | |
| Almond Oil | | 1 | | 5 | | | | | | | |
| Insect Repellent ® 3535 | 2 | | | | | | | | | | |
| Unirep ® U-18 | | | | 3 | | 5 | | | | | |
| Photonyl ® LS | 2 | 2 | | | | | | | | | |
| Panthenol | | | | 1.0 | | | | | | | |
| Bisabolol | | | | 0.2 | | | | | | | |
| Copherol ® 1250 C | | | | | 1 | | | | | | |
| MgSO$_4$ × 7H$_2$O | | | | | 1 | | | | | | |
| Bentone ® 38 | | | | | 1 | | | | | | |
| Propylene Carbonate | | | | | 0.5 | | | | | | |
| Ethanol | | | | | | | | | 8 | | |
| Butylene Glycol | | 2 | 6 | | | 2 | 5 | | | 2 | |
| Glycerin | 5 | 3 | 3 | | 5 | 3 | 2 | | 10 | 4 | |
| Water, Preservative | ad 100, q.s. | | | | | | | | | | |

TABLE 5

O/W Suncare emulsions

| Ingredients C—cream, L—lotion | 1 L | 2 C | 3 S | 4 L | 5 C | 6 L | 7 L | 8 C | 9 L | 10 C | 11 L |
|---|---|---|---|---|---|---|---|---|---|---|---|
| Eumulgin ® VL 75 | 2.0 | | | | | | | 2 | | | 2 |
| Eumulgin ® B2 | | | | 0.5 | | | | | | | |
| Tween ® 60 | | | | 0.2 | | | | | | | |
| Myrj ® 51 | | | | 0.5 | | | | | | | |
| Cutina ® E 24 | | | | 0.1 | | | | | | | |
| Hostaphat ® KL 340 N | | | | | | | | | | 1.6 | |
| Lanette ® E | | | 0.3 | | | | | | | | |
| Amphisol ® K | | | | | | | | | | 1 | |
| Sodium Stearate | | | | | | 1 | | | | | |
| Emulgade ® PL 68/50 | | 2 | 1 | | 2 | 2 | | | | | 2 |
| Imwitor 372 P | | 2 | | | | 1 | 2 | | | | |

TABLE 5-continued

O/W Suncare emulsions

| Ingredients C—cream, L—lotion | 1 L | 2 C | 3 S | 4 L | 5 C | 6 L | 7 L | 8 C | 9 L | 10 C | 11 L |
|---|---|---|---|---|---|---|---|---|---|---|---|
| Eumulgin ® SG | | 0.5 | | | | 0.1 | | 0.2 | | | |
| Eumulgin ® Prisma | 0.1 | | | | 0.75 | | | | | | |
| Tego ® Care 450 | | | | | | 2 | | | | 1 | 2.5 |
| Cutina ® PES | 2 | | 2.5 | 1 | 2.5 | | 2.5 | | 2.5 | 1.7 | 1.5 |
| Cutina ® MD | 2 | | 1 | 2 | | | 2 | | | 6 | |
| Lanette ® 14 | 1 | | | 1 | | | | 2 | | | 2 |
| Lanette ® O | 1 | 6 | | | 5 | 2 | | 2 | | | |
| Cosmedia ® DC | 1 | 1.5 | | 1 | 1 | | 2 | 2 | | | 2 |
| Antaron ® V 216 | | | 2 | | | 1.5 | | | 1 | 1 | |
| Emery 1780 | | | | | 0.5 | 0.5 | | | | | |
| Lanolin, water-free USP | | | | | | | 5 | | | | |
| Myritol ® PC | | | | | 5 | | | | | | |
| Myritol ® 331 | | | 8 | | | 6 | | 10 | | 2 | |
| Finsolv ® TN | | | 1 | | | | | 1 | | | |
| Ester as in Example 1 | 5 | 2 | 3 | 5 | 3 | 4 | 3 | 2 | 5 | 2 | 5 |
| Cetiol ® Sensoft | | 2.5 | | | 2 | | | | 3 | | |
| Cetiol ® CC | | | 2 | | | | 1 | | | | |
| Cetiol ® OE | | | 3 | | | | | | 2 | 3 | |
| Dow Corning DC ® 244 | 4 | | 1 | | | | | 2 | | | 2 |
| Dow Corning DC ® 2502 | | 1 | | | 2 | | | | | | |
| Squatol ® S | | | | | | | 4 | | | | |
| Silicone Oil Wacker AK ® 350 | | 2 | | | | | | | | | |
| Cetiol ® 868 | | | | | 2 | | 4 | | | | 2 |
| Cetiol ® J 600 | | | | | 3 | 2 | | | | 5 | |
| Mineral Oil | | | | 4 | | | | | | | |
| Cetiol ® B | | | 1 | | | | | | | 2 | |
| Eutanol ® G | | | | 2 | | | | | 4 | | |
| Eutanol ® G 16 | 4 | | | | | 4 | | | | | |
| Cetiol ® PGL | | 5 | | | | | | | | 5 | |
| Almond Oil | | | 2 | | | | | 1 | | | |
| Photonyl ® LS | | | | | 2 | | | | | 2 | |
| Panthenol | | | | | | 1 | | | | | |
| Bisabolol | | | | | | 0.2 | | | | | |
| Tocopherol/Tocopheryl Acetate | | | | | | 1 | | | | | |
| Photonyl ® LS | | | | | | | | | | | |
| Neo Heliopan ® AP (Na-salt) | | 1 | | | | | | | 1 | | |
| Neo Heliopan ® Hydro (Na-salt) | 2 | | 2.2 | | | | | | 1 | | |
| Neo Heliopan ® 303 | 3 | 5 | 9 | 4 | | | | | | | |
| Neo Heliopan ® BB | | | | | 1 | | | | | | 2 |
| Neo Heliopan ® MBC | 2 | | | 3 | | 2 | 2 | 2 | | | 1 |
| Neo Heliopan ® OS | | | | | | | | | 10 | 7 | |
| Neo Heliopan ® E 1000 | | 7.5 | | 6 | | | | | | | 6 |
| Neo Heliopan ® AV | | | 7.5 | | | 7.5 | 4 | 5 | | | |
| Uvinul ® A Plus | | | | 2 | 1 | | | | | | |
| Uvinul ® T 150 | 2 | | | | 2.5 | | | 1 | | | |
| Tinosorb ® M | | | 3 | | | | 2 | | | | 3 |
| Tinosorb ® S | | | 1 | | | | 1.5 | | | | |
| Uvasorb ® HEB | | 1 | | | 1 | | | | | | |
| Parsol ® 1789 | | 1 | 1 | | | | 2 | | 2 | 2 | |
| Zinc oxide (NDM) | 10 | | 5 | | | 10 | | 3 | | 5 | 4 |
| Eusolex ® T 2000 | | | | | 5 | | 3 | 3 | | | 4 |
| Veegum ® Ultra | 1.5 | | 0.75 | | | | | 1 | 1 | | |
| Keltrol ® T | 0.5 | | 0.25 | | | | | 0.5 | 0.5 | | |
| Cosmedia ® SP | 0.1 | 0.5 | | | 0.5 | | 0.2 | 0.2 | | 0.2 | 0.2 |
| Ultragel ™ 300 | | | | 0.2 | | 0.2 | | | | 0.1 | |
| Rheocare ® C plus | | | | | | | | | | 0.3 | 0.2 |
| Ethanol | | | | | | | | | | 10 | |
| Butylene glycol | | 2 | | 4 | 3 | | 2 | 5 | 2 | | 2 |
| Glycerin | 5 | 5 | 5 | | 3 | 3 | 2 | | 4 | | 3 |
| Preservatives, NaOH, Water | | | | | | q.s.ad 100 | | | | | |

TABLE 6

O/W suncare emulsions

| Ingredients C—cream, L—lotion | 12 L | 13 C | 14 L | 15 C | 16 L | 17 C | 18 S | 19 C | 20 C | 21 L | 22 L |
|---|---|---|---|---|---|---|---|---|---|---|---|
| Eumulgin ® VL 75 | | | 4 | | 1.8 | | | | | | |
| Eumulgin ® B2 | | | | | | | | | | 0.2 | |
| Tween ® 60 | | | | | | | | | | 0.3 | |
| Cutina ® E 24 | | | | | | | | | | 0.5 | |

TABLE 6-continued

| | O/W suncare emulsions | | | | | | | | | | |
|---|---|---|---|---|---|---|---|---|---|---|---|
| Ingredients | 12 | 13 | 14 | 15 | 16 | 17 | 18 | 19 | 20 | 21 | 22 |
| C—cream, L—lotion | L | C | L | C | L | C | S | C | C | L | L |
| Hostaphat ® KL 340 N | | | | | | | | | | | 0.5 |
| Imwitor 372 P | 2 | | | 2 | | | 2 | | 2.0 | | |
| Eumulgin ® SG | | | | 0.1 | | 0.2 | | | | | |
| Eumulgin ® Prisma | | 0.3 | 0.2 | | | | | | | | |
| Lanette ® E | | | | | | | | 0.1 | 0.5 | | |
| Amphisol ® K | 0.5 | | | | | | | 1 | | | |
| Sodium Stearate | | | | | 1 | | | | | | |
| Emulgade ® PL 68/50 | | 1.5 | | 2 | | 3 | | 2 | | | |
| Tego ® Care 450 | 1 | | | | | 2 | | 2 | 0.8 | | |
| Cutina ® PES | 2 | 2 | 2.5 | 1.5 | 2 | 2 | 2.5 | 3 | | 1.5 | 1.5 |
| Cutina ® MD | 1 | | | 4 | 1 | 3 | | | 5 | | 1 |
| Lanette ® 14 | | 2 | | | | | | | | 1 | |
| Lanette ® O | | 2 | | 2 | | | | 2 | 1 | 1 | |
| Allianz ® OPT | 1 | | | 1 | 1 | | | 2 | | | 2 |
| Cosmedia ® DC | | 1.5 | 2 | | | 1.5 | 2 | | 1.5 | 1.5 | |
| Emery ® 1780 | | | | 1 | 1 | | | | | | |
| Lanolin, water-free, USP | | | | | | 1 | 1 | | | | |
| Myritol ® PC | | | | | | | | | 3 | | |
| Myritol ® 331 | 12 | | 12 | | | 8 | 8 | | | 5 | 3 |
| Finsolv ® TN | | | | | 3 | | | | 3 | | |
| Ester as in Example 1 | 4 | 2 | 3 | 5 | 3 | 2 | 4 | 3 | 2 | 5 | 3 |
| Cetiol ® Sensoft | | | 3 | | | 5 | | | | | 2 |
| Cetiol ® CC | 2 | | | | | | 1 | | | | |
| Cetiol ® OE | | | | | 2 | | | | | | 2 |
| Dow Corning DC ® 244 | | | | | 1 | | | | | | |
| Dow Corning DC ® 2502 | | 1 | | | | | | 3 | | | |
| Ceraphyl ® 45 | | | | | | | | | | 2 | 2 |
| Silicone oil Wacker AK ® 350 | | | | | 1 | | | | | | |
| Cetiol ® 868 | | 2 | | | | | | | | | |
| Cetiol ® J 600 | | 2 | | | | | | | | | |
| Mineral Oil | | | | 5 | | | | | | | |
| Cetiol ® B | 4 | | 4 | | | | | 4 | | | |
| Eutanol ® G | | 3 | | | | 3 | | | | | |
| Eutanol ® G 16 S | 10 | | | | | | | | | | |
| Cetiol ® PGL | | | | | | | | | 2 | | |
| Photonyl ® LS | | | | | | | | | 2 | | |
| Panthenol | | | | | | 1 | | | | | |
| Bisabolol | | | | | | 0.2 | | | | | |
| Tocopherol/Tocopheryl Acetate | | | | | | 1 | | | | | |
| Neo Heliopan ® Hydro (Na-salt) | | | | | | | | | 3 | | |
| Eusolex ® OCR | 6 | | 9 | | 5 | 7 | 9 | | 4 | | 7 |
| Neo Heliopan ® AP (Na-salt) | | | | 0.5 | | 1 | | | | | |
| Neo Heliopan ® BB | | | | | | | | 1 | 1 | | 1 |
| Neo Heliopan ® MBC | | 2 | | 1 | | | | 3 | 1 | | 3 |
| Neo Heliopan ® OS | 2 | | | | | | | | 7 | | |
| Neo Heliopan ® E1000 | | 4 | | | | | | 5 | | | |
| Neo Heliopan ® AV | | 4 | 7.5 | 5 | | | | 5 | 4 | 7.5 | |
| Uvinul ® A PLUS | | | | | 1 | | 2 | | | | |
| Uvinul ® T 150 | 1 | | | | | | | | 1.3 | 1 | 1 |
| Tinosorb ® M | | | 6.5 | | | | | | 4 | | |
| Tinosorb ® S | | | 1 | | 2 | | | | | | |
| Uvasorb ® HEB | 1 | | | | | | | | | | 2 |
| Parsol ® 1789 | 1 | | | | | | | | 2 | | 1 |
| Z-Cote ® HP 1 | 7 | 2 | 5 | | | 7 | 5 | | 6 | 2 | |
| Eusolex ® T 2000 | 5 | 2 | | | 10 | | 10 | | 2 | | |
| Veegum ® Ultra | 1.5 | | 1.5 | | | 1.5 | 1.2 | | 1 | | |
| Keltrol ® T | 0.5 | | 0.5 | | | 0.5 | 0.4 | | 0.5 | | |
| Cosmedia ® SP | | | 0.2 | | | | 0.1 | | | | |
| Pemulen ® TR 2 | | 0.3 | | 0.3 | | | | 0.2 | | | |
| Ultragel ™ 300 | | | | | | | | | | 0.2 | 0.3 |
| Rheocare ® C Plus | | | | 0.3 | | 0.1 | | | | | |
| Ethanol | | 5 | | 8 | | | | | | | |
| Butylene glycol | 1 | | | 3 | 3 | | | | | 8 | 1 |
| Glycerin | 2 | 4 | 3 | 3 | | 3 | 3 | 3 | 5 | | 3 |
| Water/Preservatives/NaOH | | | | ad 100/q.s./q.s | | | | | | | |

TABLE 7

W/O suncare emulsions

| Ingredients C—cream, L—lotion | 23 C | 24 L | 25 C | 26 L | 27 C | 28 L | 29 L | 30 L | 31 L | 32 C | 34 C |
|---|---|---|---|---|---|---|---|---|---|---|---|
| Dehymuls ® PGPH | 4 | 3 | 1 | 3 | 2 | 1 | 1 | 1 | | | |
| Monomuls ® 90-O18 | | | 1 | 2 | | | | | | 2 | 4 |
| Lameform ® TGI | 2 | | | | 3 | | | | | 1 | 3 |
| Abil ® EM 90 | 2 | | | | | 4 | | 1 | | | 1 |
| Isolan GPS | | | 4 | | 3 | | | 2 | | | |
| Isolan ® PDI | | | | | | 4 | | 2 | | | |
| Zinc Stearate | 1 | | | 1 | 1 | | | 1 | | 1 | |
| Beeswax | 1 | | 5 | 1 | 3 | | | 2 | | 7 | 5 |
| Tego ® Care CG | | | | | 1 | | | | | | 0.5 |
| Cutina ® PES | | | 2 | | | 1 | 1 | | | | |
| Prisorine ® 3505 | | | 1 | | | 1 | 1 | | | | 1 |
| Cosmedia ® DC | 3 | 4 | 2 | 1 | 1 | 2 | 2 | 2 | 3 | 1 | 1 |
| Myritol ® 331 | 2 | | | | 3 | 3 | | | | | 8 |
| Finsolv ® TN | | | | 2 | | | | | | | |
| Ester as in Example 1 | 5 | 4 | 2 | 3 | 4 | 3 | 5 | 5 | 4 | 4 | 5 |
| Cetiol ® Sensoft | | | | 3 | | | 5 | | 3 | | |
| Cetiol ® CC | 5 | | | | | 2 | | | 2 | 3 | |
| Tegosoft ® DEC | | 4 | | | 2 | | | | | | |
| Cetiol ® OE | | | | | 4 | | 5 | | 2 | | |
| Dow Corning ® DC 244 | | | 3 | | | | 2 | 4 | | | |
| Dow Corning ® DC 2502 | 1 | | 1 | | 2 | 1 | | | | | 1 |
| Silicone oil Wacker AK 350 | | 1 | | 4 | | | | 3 | | | |
| Cetiol ® PGL | | | 3 | | | 4 | | 4 | | | |
| Copherol ® F 1300 | | | | | | 1 | | | | | |
| MgSO$_4$ * 7H$_2$O | | | | | | 1 | | | | | |
| Neo Heliopan ® Hydro (Na-salt) | 2 | | 2.2 | | 3 | 3 | | | 1 | | 2 |
| Neo Heliopan ® 303 | | 5 | | | | | | | 4 | | 4 |
| Uvasorb ® HEB | 1 | | | 1 | 1 | | | | | | 2 |
| Neo Heliopan ® MBC | 2 | | | | 2 | 2 | 2 | | | | |
| Uvinul ® A Plus | | | | | 2 | | | | | 3 | 3 |
| Neo Heliopan ® AP (Na-salt) | | 2 | 2 | | 1 | | | | 1 | | 6 |
| Neo Heliopan ® AV | 3 | | 4 | 6 | 4 | 7.5 | 4 | 5 | | | 1 |
| Uvinul ® T 150 | 1 | 1 | | | 2.5 | | | 1 | | | |
| Parsol ® 1789 | 2 | 1 | | | | | 2 | | | 2 | 2 |
| Zinc oxide (NDM) | | | | | | 10 | | 3 | | | 4 |
| Tinosorb ® M | | | 3 | | 3 | | | | 2 | | 2 |
| Tinosorb ® S | | | 3 | | 3 | | | | 2 | | 2 |
| Eusolex ® T Aqua | | | | 8 | | | 5 | | | | |
| Eusolex ® T 2000 | | | | | | 5 | | 3 | 3 | | 4 |
| Ethanol | | | | | | | | | 8 | | |
| Glycerin | 5 | 3 | 3 | 3 | 5 | 3 | 2 | 3 | 10 | 4 | 3 |
| Water, Preservatives | | | | | ad 100, q.s. | | | | | | |

TABLE 8

W/O suncare emulsions

| Ingredients | 12 | 13 | 14 | 15 | 16 | 17 |
|---|---|---|---|---|---|---|
| Dehymuls ® PGPH | 1 | 1 | | | 1 | 1 |
| Dehymuls ® LE | 1 | 2 | 1 | 1 | 1 | 1 |
| Abil ® EM 90 | | | | 4 | | |
| Isolan GPS | 3 | | 1 | 1 | | |
| Isolan ® PDI | | | 4 | | 2 | |
| Zinc Stearate | | | 1 | | | 1 |
| Beeswax | | 1 | | | 5 | |
| Cutina ® PES | | 1 | | 1 | | |
| Prisorine ® 3505 | | | 1 | 1 | | |
| Cosmedia ® DC | 4 | 1 | 2 | 2 | 2 | 3 |
| Myritol ® 331 | | | 3 | | | |
| Finsolv ® TN | | 2 | | | | |
| Ester as in Example 1 | 4 | 3 | 3 | 5 | 5 | 4 |
| Cetiol ® CC | | | 2 | | | 2 |
| Cetiol ® Sensoft | | 2 | | 2 | | 4 |
| Tegosoft ® DEC | 4 | 3 | | 5 | | |
| Cetiol ® OE | 2 | | | 5 | | |
| Dow Corning ® DC 244 | | | | | 2 | 4 |
| Dow Corning ® DC 2502 | | | 1 | | | |
| Silicone oil Wacker AK 350 | 1 | 4 | | | 3 | |
| Cetiol ® PGL | 3 | | 4 | | | 4 |
| Copherol ® F 1300 | | | | 1 | | |
| MgSO$_4$ * 7H$_2$O | | | | 1 | | |
| Neo Heliopan ® Hydro (Na-salt) | | | 3 | | | 1 |
| Neo Heliopan ® 303 | 5 | | | | | 4 |
| Uvasorb ® HEB | 1 | | | | | |
| Neo Heliopan ® MBC | | | 2 | 2 | 2 | |
| Uvinul ® A Plus | | | | | | 3 |
| Neo Heliopan ® AP (Na-salt) | 2 | | | | | 1 |
| Neo Heliopan ® AV | | 6 | 7.5 | 4 | 5 | |
| Uvinul ® T 150 | 1 | | | | 1 | |
| Parsol ® 1789 | 1 | | | 2 | | 2 |
| Zinc oxide NDM | | | 10 | | 3 | |
| Tinosorb ® M | 3 | 3 | | | 2 | |
| Tinosorb ® S | 3 | 3 | | | 2 | |
| Eusolex ® T Aqua | | | | | 5 | |
| Eusolex ® T 2000 | | | | 3 | 3 | |
| Glycerin | 3 | 3 | 3 | 2 | 3 | 10 |
| Water, Preservatives | | | ad 100, q.s. | | | |

TABLE 9

Decorative cosmetics - O/W foundations

| Ingredients | 1 | 2 | 3 | 4 | 5 | 6 | 7 | 8 |
|---|---|---|---|---|---|---|---|---|
| Cutina ® GMS-SE | 5.5 | | | | | | | 3.0 |
| Emulgade ® PL 68/50 | | 5.0 | | | 2.0 | | | |
| Eumulgin ® VL 75 | | | 3.0 | | | 5.0 | | |
| Tego Care ® 450 | | | | | | 2.0 | 2.0 | |
| Codesta ® F-50 | | | | | 6.0 | | | |
| Amphisol ® K | | | | 2.0 | | | | |
| Lanette ® E | | 0.25 | | | | | | |
| Eumulgin ® SG | | | | | 1.0 | | 1 | |
| Eumulgin ® Prisma | | | | | | 1.0 | | 0.75 |
| Imwitor 372 P | | 2 | | | | | 1 | |
| Cutina ® FS 45 | 1.5 | | | | | | | |
| Eumulgin ® B 2 | | | 2.0 | | | | | |
| Cutina ® PES | 2.0 | 1.0 | 2.0 | 4.0 | 2.0 | 1.0 | 2.5 | 2.0 |
| Lanette ® O | | | 2.0 | | | | | 1.0 |
| Cutina ® MD | | 0.5 | 3.0 | 3.0 | | | | |
| Cetiol ® LC | 4.0 | | | | | | | |
| Cosmedia ® DC | 0.5 | | | 1.0 | | | | 1.0 |
| Ester as in Example 1 | 4.0 | 5.0 | 4.0 | 2.0 | 7.0 | 5.0 | 10.0 | 4.0 |
| Cetiol ® Sensoft | 2.0 | | | | 3.0 | | | 2.0 |
| Tegosoft ® DEC | | 5.0 | | 2.0 | | 2.0 | | 2.0 |
| Cetiol ® CC | | | 2.0 | | 2.0 | | | |
| Dow Corning ® 245 | | 2.0 | | 2.0 | | | | |
| Eutanol ® G 16 | 4.0 | | | | | 3.0 | | |
| Myritol ® 331 | | 5.0 | | | 2.0 | 2.0 | 5.0 | |
| Uvinul ® T 150 | | | | 0.5 | | | | 0.5 |
| Uvasorb ® HEB | 2.0 | | | | | | 1.0 | 1.0 |
| Tinosorb ® M | | | 2.0 | | | | | 2.0 |
| Tinosorb ® S | | | | 3.0 | | | | 2.0 |
| Neo Heliopan ® AV | | | | | 2.0 | | 2.0 | |
| Heo Heliopan ® AP | | | | | 1.0 | | 1.0 | |
| Uvinul ® A Plus | | | 1 | | | | 2.0 | 2.0 |
| Microna ® Matte White | 5.0 | 5.0 | | 5.0 | 5.0 | 5.0 | | 5.0 |
| Microna ® Matte Black | 0.3 | 0.3 | 0.1 | 0.3 | 0.3 | 0.3 | 0.4 | 0.3 |

TABLE 9-continued

Decorative cosmetics - O/W foundations

| Ingredients | 1 | 2 | 3 | 4 | 5 | 6 | 7 | 8 |
|---|---|---|---|---|---|---|---|---|
| Microna ® Matte Yellow | 3.0 | 3.0 |  | 3.0 | 3.0 | 3.0 | 2.0 | 3.0 |
| Microna ® Matte Red | 0.6 | 0.6 | 1.0 | 0.6 | 0.6 | 0.6 | 1.0 | 0.6 |
| Ronasphere ® | 1.0 | 1.0 |  | 1.0 | 1.0 | 1.0 |  | 1.0 |
| Pigment White 6 |  |  |  | 6.0 |  |  | 6.0 |  |
| Dry Flow PC |  |  |  |  |  |  | 2.0 | 2.0 |
| Glycerin | 5.0 | 5.0 | 3.0 | 5.0 | 5.0 | 5.0 | 3.0 |  |
| Cosmedia ® SP |  |  | 0.3 |  | 0.2 |  |  |  |
| Water, de-ionized, Preservative | ad 100 | | | | | | | |

TABLE 10

Decorative cosmetics - W/O foundations

| Ingredients | 1 | 2 | 3 | 4 | 5 | 6 | 7 | 8 |
|---|---|---|---|---|---|---|---|---|
| Dehymuls ® PGPH | 5.5 |  | 4.0 |  |  |  |  | 3.0 |
| Lameform ® TGI |  | 5.0 |  |  | 2.0 |  |  |  |
| Abil ® EM 90 |  |  |  | 3.0 |  | 5.0 |  |  |
| Isolan ® GI 34 |  |  |  |  |  |  | 2.0 | 2.0 |
| Isolan ® PDI |  |  |  | 1.0 | 6.0 |  |  |  |
| Isolan ® GPS | 1.0 | 2.0 |  | 1.0 |  |  |  |  |
| Admul ® WOL 1403 |  |  |  | 2.0 |  |  |  |  |
| Dehymuls ® HRE 7 |  | 1.0 |  |  | 1.0 | 1.0 |  |  |
| Monomuls ® 90-O18 | 1.5 |  |  |  |  |  |  | 2.0 |
| Cutina ® PES | 2.0 | 1.0 | 2.0 | 4.0 | 2.0 | 1.0 | 2.5 | 2.0 |
| Cera Bellina |  |  | 2.0 |  |  |  |  | 2.0 |
| Beeswax |  |  | 2.0 |  |  | 2.0 |  | 1.0 |
| Microcrystalline Wax |  | 1.5 | 3.0 | 3.0 |  |  |  |  |
| Cetiol ® LC | 4.0 | 5.0 |  |  |  |  |  |  |
| Cosmedia ® DC | 1.0 |  |  |  | 0.5 |  | 1.0 |  |
| Ester as in Example 1 | 4.0 | 2.0 | 2.0 | 4.0 | 5.0 | 5.0 | 5.0 | 4.0 |
| Cetiol ® Sensoft |  | 2.0 |  |  | 2.0 |  | 5.0 |  |
| Tegosoft ® DEC |  | 3.0 |  |  |  | 2.0 |  |  |
| Cetiol ® CC |  |  |  | 2.0 |  |  |  | 2.0 |
| Dow Corning ® 245 |  | 2.0 |  | 2.0 |  |  |  | 2.0 |
| Eutanol ® G 16 | 4.0 |  |  |  | 3.0 | 3.0 |  |  |
| Myritol ® 331 |  | 5.0 |  |  | 2.0 |  | 5.0 |  |
| Uvinul ® T 150 |  |  |  | 0.5 |  |  |  | 0.5 |
| Uvasorb ® HEB |  |  | 2.0 |  |  |  | 1.0 | 1.0 |
| Tinosorb ® M |  |  | 2.0 |  |  |  |  | 2.0 |
| Tinosorb S |  |  |  | 3.0 |  |  |  | 2.0 |
| Neo Heliopan ® AV |  |  |  | 2.0 |  |  | 2.0 |  |
| Heo Heliopan ® AP |  |  |  | 1.0 |  |  | 1.0 |  |
| Uvinul ® A plus |  |  | 1.0 |  |  |  | 2.0 | 2.0 |

TABLE 10-continued

Decorative cosmetics - W/O foundations

| Ingredients | 1 | 2 | 3 | 4 | 5 | 6 | 7 | 8 |
|---|---|---|---|---|---|---|---|---|
| Microna ® Matte White | 5.0 | 5.0 |  | 5.0 | 5.0 | 5.0 |  | 5.0 |
| Microna ® Matte Black | 0.3 | 0.3 | 0.1 | 0.3 | 0.3 | 0.3 | 0.4 | 0.3 |
| Microna ® Matte Yellow | 3.0 | 3.0 | 3.5 | 3.0 | 3.0 | 3.0 | 2.0 | 3.0 |
| Microna ® Matte Red | 0.6 | 0.6 | 1.0 | 0.6 | 0.6 | 0.6 | 1.0 | 0.6 |
| Ronasphere ® | 1.0 | 1.0 |  | 1.0 | 1.0 | 1.0 |  | 1.0 |
| Pigment White 6 |  |  |  | 6.0 |  |  | 6.0 |  |
| Dry Flow PC |  |  |  |  |  |  | 2.0 | 2.0 |
| Glycerin | 5.0 | 5.0 | 3.0 | 5.0 | 5.0 | 5.0 | 3.0 |  |
| Water, de-ionized, Preservative | ad 100 | | | | | | | |

TABLE 11

Decorative cosmetics - lipsticks

| Ingredients | 1 | 2 | 3 | 4 |
|---|---|---|---|---|
| Cutina ® LM conc |  |  | 10.0 | 36.0 |
| Candelilla Wax | 9.39 | 5.0 | 10.0 |  |
| Carnauba wax | 2.85 | 7.0 | 5.0 |  |
| Beeswax | 1.86 | 5.0 | 4.0 |  |
| Cutina ® PES | 3.2 | 5.0 | 6.4 | 4.5 |
| Cetiol ® MM |  |  | 5.0 |  |
| Cosmedia ® DC | 5.0 | 4.0 | 2.0 | 6.0 |
| Ester as in Example 1 | 7.0 | 6.0 | 3.0 | 5.0 |
| Cetiol ® Sensoft | 2.0 |  | 4.5 |  |
| Tegosoft ® DEC | 3.0 | 3.0 | 3.0 | 5.0 |
| Eutanol ® G | 10.97 | 12.0 | 12.0 |  |
| Fitoderm ® |  |  |  | 4.0 |
| Monomuls ® 90L 12 |  | 3.0 |  |  |
| Dehymuls ® PGPH |  | 4.0 |  |  |
| Castor Oil | 11.0 | 15.5 | 14.5 | 30.0 |
| Copherol ® F 1300 | 1.0 | 1.0 | 1.0 | 1.0 |
| Cosmetic white C47056 | 5.0 | 2.0 | 5.0 |  |
| FDC Yellow 6 Al Lake C705270 | 7.0 | 7.0 | 8.0 |  |
| DC Red 7 Ca Lake C 19003 | 6.0 | 4.5 | 1.1 | 2.9 |
| Irodin 100 Silverpearl |  |  |  | 9.6 |
| Hydagen ® CMF |  | 10.0 |  |  |
| Irwinol ® LS 9319 | 1.0 |  | 3.0 |  |
| Mineral Oil | 12.8 |  |  |  |
| Petrolatum | 6.84 | 3.0 |  |  |
| Ceresin | 2.75 |  |  |  |
| Microcrystalline Wax | 2.45 |  |  |  |
| Colophane Claire type Y | 1.89 |  |  |  |

TABLE 12

Antiperspirant/deodorant concepts

| Ingredients (INCI) | 1 | 2 | 3 | 4 | 5 | 6 | 7 |
|---|---|---|---|---|---|---|---|
| Glyceryl Stearate, Ceteareth-20, Ceteareth-12, Cetearyl Alcohol, Cetyl Palmitate (Emulgade ® SE) | 6 |  |  | 4.5 |  | 6 |  |
| Ceteareth-20 (Eumulgin ® B2) |  |  |  |  | 1 |  |  |
| Glyceryl Stearate Citrate (Imwitor 372 P) |  | 4.0 |  |  |  |  |  |
| Polyglyceryl-3 Diisostearate (Lameform ® TGI) |  |  | 3 |  |  |  |  |
| Cocoglycerides (Novata ® AB) |  |  |  |  |  |  | 4 |
| Stearyl alcohol (Lanette ® 18) |  |  |  |  | 10 |  |  |
| Hydrogenated Castor Oil (Cutina ® HR) |  |  |  |  |  | 3.7 | 6.5 |
| Polyglyceryl-2 Dipolyhydroxystearate (Dehymuls ® PGPH) |  |  |  | 1 |  |  |  |
| Sodium Stearoyl Glutamate (Eumulgin ® SG) |  | 0.2 |  |  |  |  |  |
| Disodium Cetearyl Sulfosuccinate (Eumulgin ® Prisma) | 0.3 |  |  |  |  |  |  |
| Sodium Cetearyl Sulfate (Lanette ® E) |  |  |  |  |  |  | 0.3 |
| Pentaerythrityl Distearate (Cutina ® PES) | 5 | 1 | 2 | 1 | 4.7 | 5 | 4 |
| Behenyl Alcohol (Lanette ® 22) | 2 | 1 |  |  |  | 4 |  |
| Ester as in Example 1 | 4 | 4 | 5 | 3 | 4 | 3 | 5 |
| Propylheptyl Caprylate (Cetiol ® Sensoft) |  | 2 |  |  | 20 |  | 10 |
| Dicaprylyl Carbonate (Cetiol ® CC) |  |  |  |  | 2 |  |  |

TABLE 12-continued

Antiperspirant/deodorant concepts

| Ingredients (INCI) | 1 | 2 | 3 | 4 | 5 | 6 | 7 |
|---|---|---|---|---|---|---|---|
| Dicaprylyl Ether (Cetiol ® OE) | 2 | | | 2 | 5 | 3 | 4 |
| Cocoglycerides (Myritol ® 331) | | | | | | | |
| Diethylhexylcyclohexane (Cetiol ® S) | | | | 5 | 14.7 | | 25 |
| Cyclopentasiloxane | 3 | | 5 | | 14 | 3 | 14 |
| Cyclopentasiloxane and Dimethicone/Vinyldimethicone Crosspolymer SFE 839 (GE Bayer) | | | 3 | | | | |
| Dimethicone AK 350 | 1 | 2 | | | | | |
| Hydrogenated Dimer Dilinoleyl/Dimethylcarbonate Copolymer (Cosmedia ® DC) | 0.5 | | 1 | 1.5 | 1 | 2 | 1 |
| Triethyl Citrate (Hydagen ® C.A.T) | | | | 2 | | | |
| Tocopheryl Acetate | | | | | 1 | | |
| Aluminium Zirconium Tetrachlorohydrex GLY (Rezal 36) | 30 | | 40 | | 22.9 | 30 | 25 |
| Aluminum Chlorhydrate (Locron L) | | 20 | | 10 | | | |
| Chitosan (Hydagen ® DCMF) | 0.05 | | | | | | |
| Glycolic Acid | 0.02 | | | | | | |
| Glycerin | | | 5 | 5 | | | |
| Propylene Carbonate (Fluka) | | | | | | | 0.5 |
| Quaternium-18 Hectorite (Bentone 18) | | | | | | | 1 |
| Polyquaternium-37 (Ultragel 37) | | 5 | | | | | |
| Talc (Merck) | | | | | | 5 | 5 |
| MgSO$_4$ × 7H$_2$O | | | | 1 | | | |
| Water, Perfume, Preservatives | q.s. | q.s. | q.s. | q.s. | q.s. | q.s. | q.s. |

1/2 - antiperspirant/deodorant cream,

3 - antiperspirant cream (W/O),

4 - antiperspirant/deodorant spray,

5 - antiperspirant stick with vitamin E,

6 - antiperspirant cream,

7 - antiperspirant cream "soft solid"

TABLE 13

Haircare conditioner

| Ingredients (INCI) | 1 | 2 | 3 | 5 | 6 | 7 | 8 |
|---|---|---|---|---|---|---|---|
| Structure ® XL(*) (Hydroxypropyl Starch Phosphate) | 5.0 | 5.0 | 5.0 | 4.0 | | | |
| Emulgade ® Sucro (Sucrose Polystearate, Hydrogenated Polyisobutene) | | | | | 1.0 | 1.0 | 1.0 |
| Dehyquart ® L 80 (Dicocoylethyl Hydroxyethylmonium Methosulfate, Propylene Glycol) | 2.6 | 1.3 | 2.0 | | | 0.5 | 0.5 |
| Dehyquart ® F 75 (Distearoylethyl Hydroxyethylmonium Methosulfate, Cetearyl Alcohol) | | | 2.0 | | | | |
| Dehyquart ® C 304 (Aqua, Cocamidopropyl-trimonium Methosulfate, Propylene Glycol) | | | | 3.7 | | 4.0 | 4.0 |
| Ester as in Example 1 | 1.0 | 3.0 | 1.0 | 0.5 | 2.0 | 1.5 | 1.5 |
| Dehyquart ® A CA (Cetrimonium Chloride) | | | | | 4.0 | | |
| DC 200(***) (Dimethicone) | | | | 0.5 | | | |
| Lanette ® O (Cetearyl Alcohol) | | | 1.0 | | 4.0 | | |
| Lamesoft ® TM Benz (Glycol Distearate, Coco Glucoside, Glyceryl Oleate, Glyceryl Stearate) | 4.0 | | | 1.0 | | | |
| Gluadin ® WLM (Hydrolyzed Wheat Protein) | 1.0 | 1.0 | | 1.0 | | | 0.3 |
| Glycerin | | | 0.5 | | | | |
| Gluadin ® Soy (Hydrolyzed Wheat Protein) | | 0.5 | | | | | |
| Cocoa Butter(**) Theobroma Cacao (Cocoa) Seed Butter | | | 0.5 | | | | |
| Herbalia Balm Mint (Melissa Officinalis, Maltodextrin, Silica) | | 0.01 | | | | | 0.02 |
| Ultragel ™ 300 (Polyquarternium-37) | | | | | | 0.2 | 0.2 |

TABLE 13-continued

| | Haircare conditioner | | | | | | |
|---|---|---|---|---|---|---|---|
| Ingredients (INCI) | 1 | 2 | 3 | 5 | 6 | 7 | 8 |
| Perfume, preservative | q.s. | q.s. | q.s. | q.s. | q.s. | q.s. | q.s. |
| Deionized water | Up to 100 | Up to 100 | Up to 100 | Up to 100 | Up to 100 | Up to 100 | Up to 100 |

(*)National Starch,
(**)Nederland,
(***)Dow Corning;
pH adjusted to 3.5-5.0

TABLE 14

| | Haircare conditioners | | | |
|---|---|---|---|---|
| Ingredients (INCI) | 9 | 10 | 11 | 12 |
| Dehyquart ® L 80 (Dicocoylethyl Hydroxyethylmonium Methosulfate, Propylene Glycol) | 1.3 | 1.3 | | 1.0 |
| Dehyquart ® F 75 (Distearoylethyl Hydroxyethylmonium Methosulfate, Cetearyl Alcohol) | 1.3 | 1.3 | 1.3 | 1.5 |
| Lanette ® O (Getearyl Alcohol) | 5.0 | 5.0 | 4.0 | 4.5 |
| Ester as in Example 1 | 1.0 | 1.0 | 1.0 | 0.5 |
| Cetiol ® SB 45 *Butyrospermum Parkii* (Shea Butter) | 4.0 | 4.0 | 2.0 | 4.5 |
| Gluadin ® Almond (Hydrolyzed Sweet Almond Protein) | | | 0.1 | 0.5 |
| ASCO BTAC (Behentrimonium Chloride) | | | 1.3 | |
| DC 949 (****)Amodimethicone, Trideceth-12, Cetrimonium Chloride | | 1.0 | | |
| Cegesoft ® PFO (*Passiflora Incarnata* Seed Oil) | | | 2.0 | |
| Aloveria ® (*Aloe Barbadensis*) | 0.1 | | | |
| Sphingoceryl ® Veg: Octyldodecanol, Hydrogenated Coco Glycerides, *Helianthus Annuus* (Sunflower) Seed Extract | 1.0 | | | |
| Copherol ® 1250 (Tocopheryl Acetate) | 0.2 | | | |
| Ultragel ™ 300 (Polyquartemium-37) | | 0.1 | | 0.2 |
| Perfume, preservative | q.s. | q.s. | q.s. | q.s. |
| Deionized water | Up to 100 | Up to 100 | Up to 100 | Up to 100 |

(****)Dow Corning; pH adjusted to 3.5-5.0

TABLE 15

| | Haircare conditioner | | | |
|---|---|---|---|---|
| | 13 | 14 | 15 | 16 |
| Ester as in Example 1 | 10 | 10.6 | 43.6 | 30 |
| Myritol ® 318 (Caprylic Capric Triglyceride) | | | 43.6 | 20 |
| Cetiol ® ISL (Isostearyl Lactate) | | | | 40 |
| DC 1501 (*) (Cyclomethicone, Dimethiconol) | 69.5 | | | |
| Emery ® 3004 (Hydrogenated Polydecene) | | 67.8 | | |
| DC 345 (*) Cyclomethicone | 20 | | | |
| Versagel MC 750 (**) Isohexadecene, Ethylene/Propylene/Styrene Copolymer, Butylene/Ethylene/Styrene Copolymer | | 21.3 | | |
| DC 556 (*) Phenyl Trimethicone | 0.5 | | | |
| Wacker HDK H 20 (***): Phenyl Trimethicone | | | 12.5 | 10 |
| Ultragel ™ 300 (Polyquartemium-37) | 0.2 | | | 0.2 |
| Perfume | q.s. | q.s. | q.s. | q.s. |

(*) Dow Corning,
(**) Penreco,
(***) Wacker

TABLE 16

| | Haircare conditioners | | | | |
|---|---|---|---|---|---|
| Ingredients (INCI) | 17 | 18 | 19 | 20 | 21 |
| Cetearyl Alcohol (Lanette ® O) | 5.0 | 4.5 | | | |
| Glyceryl Stearate (Cutina ® MD) | 4.0 | | | 14.5 | |
| Cetearyl Alcohol (Lanette ® O) | | | | 7.0 | |
| Hydrogenated Castor Oil (Cutina ® HR) | | | | 2.5 | |
| Cetyl Palmitate (Cutina ® CP) | | 0.3 | | 7.0 | |
| Paraffin Oil | | | | 23.5 | |
| Vaseline | | | | 32.5 | |
| Wacker Silicon Oil AK 350 | | | | 0.5 | |
| Ester as in Example 1 | 3.0 | 0.2 | 1.5 | 2.0 | 5.0 |
| Oleyl Erucate (Cetiol ® J 600) | 2.0 | | | | |
| PEG-7 Glyceryl Cocoate (Cetiol ® HE) | | | | | 20.0 |
| Dimethicone (Dow Corning 200) | | 0.2 | | | |
| Ceteareth-12 (Eumulgin ® B1) | 1.0 | | | | |
| Ceteareth-20 (Eumulgin ® B2) | | 0.4 | | | |
| Ceteareth-30 (Eumulgin ® B3) | | | | | 14.0 |
| Cetoleth-20 (Eumulgin ® O20) | | | | 5.0 | |
| Glycerin, Glyceryl Polyacrylate (Hispagel ® 200) | | | 36.7 | | |
| Lauryl Glucoside (Plantacare ® 1200 UP) | | | | 5.0 | |
| Laureth-7 Citrate (Plantapon ® LC 7) | | 0.7 | 1.0 | | |

TABLE 16-continued

Haircare conditioners

| Ingredients (INCI) | 17 | 18 | 19 | 20 | 21 |
|---|---|---|---|---|---|
| *Glycine Soya* (Soybean) Sterols (Generol ® 122 N) | 0.5 | | | | |
| Hydrogenated Dimer Dilinoleyl/Dimethylcarbonate Copolymer (Cosmedia ® DC) | | 1.0 | | | |
| Glycerin | | 3.0 | | | |
| Cocamide MEA (Comperlan ® 100) | | | | 2.5 | |
| Cetrimonium Chloride (Dehyquart ® A) | 3.0 | 4.0 | | | |
| Hydrolyzed Keratin (Nutrilan ® Keratin W) | 2.0 | | | | |
| PVP/VA (Luviskol ® VA 64) | | | 4.5 | | |
| PEG-90M (Polyox ® WSR-301) | | | 0.25 | | |
| Hydroxypropyl Methylcellulose (Methocel ® E4M Premium EP) | | | 0.6 | | |
| Dicocoylethyl Hydroxyethylmonium Methosulfat, Propylene Glycol (Dehyquart ® L 80) | | | | 0.6 | |
| Triethanolamine | | | | 1.0 | |
| CaCl$_2$ * 2 H$_2$O | | | 0.1 | | |
| Ethanol | | | | 12.0 | |
| Polyquarternium-37 (Ultragel ™ 300) | 0.2 | | | | |
| Water, Perfume, Preservatives | q.s. | q.s. | q.s. | q.s. | q.s. |

TABLE 17

Rinse-off concepts

| Ingredients (INCI) | 1 | 2 | 3 | 4 | 5 | 6 |
|---|---|---|---|---|---|---|
| Sodium Laureth Sulfate (Texapon ® N 70) | 12.9 | | 12.3 | 14.3 | 14.3 | |
| Cocamidopropyl Betaine (Dehyton ® PK 45) | 7.7 | | 5.4 | 5.4 | 5.4 | |
| Laureth-7 Citrate (Plantapon ® LC 7) | 10.0 | 2.5 | | | | 10.0 |
| Guar Hydroxypropyltrimonium Chloride (Cosmedia ® Guar C 261N) | | | 0.25 | 0.2 | | |
| Polyquaternium-7 | | | | 2.5 | | |
| Polyquaternium-10 | | | | | 0.15 | |
| Polyquaternium-44 | | | 1.5 | | 1.5 | |
| Glycol Distearate, Laureth-4, Cocamidopropyl Betaine (Euperlane ® PK 4000) | | | 10.0 | 2.0 | 2.0 | |
| PEG-40 Hydrogenated Castor Oil (Eumulgin ® HRE 40) | | 7.5 | | | | |
| Mineral Oil | | | | | | 55.0 |
| (Propylheptyl Caprylate) Cetiol ® Sensoft | | | | | | 29.0 |
| Ester as in Example 1 | 1.0 | 2.0 | 1.0 | 0.5 | 0.5 | 5.0 |
| Lauryl Alcohol | | | 0.5 | 0.5 | 0.5 | |
| Sodium Chloride | | | adjust viscosity | | | |
| Ethanol | | 25.0 | | | | |
| Water, Perfume, Preservatives | q.s. | q.s. | q.s. | q.s. | q.s. | q.s. |
| pH (adjusted with NaOH or citric acid) | 5.5 | 6.0 | 5.5 | 5.7 | 5.4 | 5.5 |

TABLE 18

Rinse-off concepts

| Ingredients (INCI) | 7 | 8 | 9 | 10 | 11 | 12 |
|---|---|---|---|---|---|---|
| MIPA-Laureth Sulfate, Laureth-4, Propylene Glycol (Texapon ® W 90) | 40.7 | 28.3 | 28.3 | 28.3 | 28.3 | |
| Sodium Laureth Sulfate (Texapon ® N 70) | | | | | | 10.9 |
| Coco-Glucoside (Plantacare ® 818 UP) | | | | | | 6.9 |
| Laureth-7 Citrate (Plantapon ® LC 7) | 5.0 | 28.3 | 28.3 | 28.3 | 28.3 | |
| Laureth-2 (Mergital ® LM2 DEO) | 10.0 | | | | | |
| PEG-7 Glyceryl Cocoate (Cetiol ® HE) | 1.1 | | | | | |
| Soya oil | | | 20.7 | | | |
| Almond Oil | | | | | | 0.5 |
| Paraffinum Liquidum | | | | | 7.0 | 23.0 |
| Cyclomethicone ((Dow Corning ® 245) | | | | | | |
| Dimethicone Copolyol (Dow Corning ® 193) | | | | 1.0 | | |
| Olus (Cegesoft ® PS6) | 22.0 | | | | | 10.0 |
| Ester as in Example 1 | 20.0 | 41.4 | 20.7 | 40.4 | 34.4 | 15.0 |
| Acrylates Copolymer (Carbopol ® Aqua) | | | | | | 4.0 |
| Acrylates/C10-30 Alkyl Acrylate Crosspolymer (Pemulen ® TR-1) | | | | | | 0.5 |
| AMP ® 95 | 1.2 | | | | | |
| Poloxamer ® 101 | | 2.0 | 2.0 | 2.0 | 2.0 | |
| Water | | | | | | q.s. |

APPENDIX

Ingredients

AMP-95, INCI: Aminomethyl Propanol, Dow Chemical Co; Abil® EM 90; INCI: Cetyl Dimethicone Copolyol; Tego Cosmetics (Goldschmidt); Allianz® OPT; INCI: Acrylates/C12-22 Alkyl Methacrylate Copolymer; Rohm and Haas; Amphisol® K; INCI: Potassium Cetyl Phosphate; Hoffmann La Roche; Admul® WOL 1403, INCI: Polyricinoleate of polyglycerol, Quest; Antaron® V 220; INCI: PVP/Eicosene Copolymer; GAF General Aniline Firm Corp. (IPS-Global); Antaron® V 216; INCI: PVP/Hexadecene Copolymer: GAF General Aniline Firm Corp. (IPS-Global); Arlacel® 83; INCI: Sorbitan Sesquioleate, Uniqema (ICI Surfactants); Arlacel® P 135, INCI: PEG-30 Dipolyhydroxystearate, Uniqema (ICI Surfactants); Bentone® 38, INCI: Quatemium-18 Hectorite, Rheox (Elementis Specialties); Carbopol® 980, Carbomer, Goodrich; Carbopol® 2984, INCI: Carbomer, Noveon, Inc.; Carbopol® ETD 2001, INCI: Carbomer, Noveon, Inc.; Carbopol® Ultrez 10, INCI: Carbomer; Noveon, Inc.; Cegesoft® C 17, Myristyl Lactate, Cognis GmbH; Cegesoft® PFO, INCI: Passiflora Incarnata (EU); Cognis GmbH; Cegesoft® PS 6, INCI: Olus, Cognis GmbH, Cegesoft® SH, INCI: Shorea Stenoptera Seed Butter Cognis GmbH; Ceraphyl® 45, INCI: Diethylhexyl Malate, International Specialty Products; Cetiol® 868, INCI: Ethylhexyl Stearate, Hersteller: Cognis GmbH; Cetiol® A, INCI: Hexyl Laurate, Cognis GmbH; Cetiol® B, INCI: Dibutyl Adipate, Cognis GmbH; Cetiol® CC, INCI: Dicaprylyl Carbonate; Cognis GmbH; Cetiol® J 600, INCI: Oleyl Erucate, Cognis GmbH; Cetiol® LC, INCI: Coco-Caprylate/Caprate, Cognis GmbH; Cetiol® MM, INCI: Myristyl Myristate, Cognis GmbH; Cetiol® OE, INCI: Dicaprylyl Ether, Cognis GmbH; Cetiol® PGL, INCI: Hexyldecanol, Hexyldecyl Laurate, Cognis GmbH; Cetiol® 5, INCI: Diethylhexylcyclohexane, Cognis GmbH; Cetiol® SB 45, INCI: Shea Butter Butyrospermum Parkii (Linne), Cognis GmbH; Cetiol® SN, INCI: Cetearyl Isononanoate, Cognis GmbH; Copherol® F. 1300 C, INCI: Tocopherol, Cognis GmbH; Copherol 1250 C, INCI: Tocopberyl Acetate, Cognis GmbH; Cosmedia® DC, INCI: Hydrogenated Dimer Dilinoleyl/Dimethylcarbonate Copolymer; Cognis GmbH; Cosmedia® SP, INCI: Sodium Polyacrylate; Cognis GmbH; Cutina® E 24, INCI: PEG-20 Glyceryl Stearate; Cognis GmbH; Cutina® HR, INCI: Hydrogenated Castor Oil, Cognis GmbH; Cutina® MD, INCI: Glyceryl Stearate, Cognis GmbH; Cutina® PES, INCI: Pentaerythrityl Distearate, Cognis GmbH; Cutina FS-45, INCI: Palmitic Acid, Stearic Acid, Cognis GmbH; Cutina® GMS-SE, INCI Glyceryl Stearate SE, Cognis GmbH; Cutina® LM cone, INCI: Polyglyceryl-2 Dipolyhydroxystearate, Octyldodecanol, Copernicia Cerifera (Carnauba) Wax, Euphorbia Cerifera (Candelilla) Wax, Beeswax, Cetearyl Glucoside, Cetearyl Alcohol, Cognis GmbH; Dehymuls® FCE, INCI: Dicocoyl Pentaerythrityl Distearyl Citrate, Cognis GmbH; Dehymuls® HRE 7, INCEPEG-7 Hydrogenated Castor Oil, Cognis GmbH; Dehymuls® PGPH, INCI: Polyglyceryl-2 Dipolyhydroxystearate, Cognis GmbH; Crodesta® F-59, INCI Sucrosedistearate, Croda; Dehymuls® LE, INCI: PEG-30 Dipolyhydroxystearate, Cognis GmbH; Dow Corning® 244 Fluid, INCI: Cyclomethicone, Dow Corning; Dow Corning® 246 Fluid, Cyclopentasiloxane, Dow Corning; Dow Corning® 2502, INCI: Cetyl Dimethicone, Dow Corning; Dow Corning DC® 245 INCI: Cyclopentasiloxane, Dow Corning, Dehyquart® C 4046, INCI: Cetearyl Alcohol, Dipalmitoylethyl Hydroxyethylmonium Methosulfate, Ceteareth-20, Cognis GmbH; Dry® Flo Plus, INCI: Aluminium Starch Octenylsuccinate, National Starch; Dry® Flo PC, INCI: Aluminum Starch Octenylsuccinate, Akzo Nobel; Elfacos® ST 37, INCI: PEG-22 Dodecyl Glycol Copolymer, Akzo-Nobel; Elfacos® ST 9, INCI: PEG-45 Dodecyl Glycol Copolymer, Akzo-Nobel; Emery® 1780, INCI: Lanolin Alcohol, Cognis Corp.; Emulgade® CM, INCI: Cetearyl Isononanoate and Ceteareth-20 and Cetearyl Alcohol and Glyceryl Stearate and Glycerin and Ceteareth-12 and Cetyl Palmitate, Cognis GmbH; Emulgade® PL 68/50, INCI: Cetearyl Glucoside, Cetearyl Alcohol, Cognis GmbH; Emulgade® SE-PF, INCI: Glyceryl Stearate (and) Ceteareth-20 (and) Ceteareth-12 (and) Cetearyl Alcohol (and) Cetyl Palmitate; Cognis GmbH, Emulgade® SUCRO, INCI: Sucrose Polystearate (and) Hydrogenated Polyisobutene, Cognis GmbH; Eumulgin® B1, INCI: Ceteareth-12, Cognis GmbH, Eumulgin® B 2, INCI: Ceteareth-20, Cognis GmbH; Eumulgin® HRE. 40, INCI: PEG-40 Hydrogenated Castor Oil, Cognis GmbH; Eumulgin® Prisma INCI: Disodium Cetearyl Sulfosuccinate; Eumulgin® SG, INCI: Sodium Stearoyl Glutamate, Cognis GmbH; Eumulgin® VL 75, INCI: Lauryl Glucoside (and) Polyglyceryl-2 Dipolyhydroxystearate (and) Glycerin; Cognis GmbH; Eusolex® OCR, INCI: Octocrylene, Merck; Eusolex® T 2000, INCI: Titanium Dioxide, Alumina, Simethicone, Merck; Eusolex® AQUA, INCI: Water and Titanium Dioxide and Alumina and Sodium Metaphosphate and Phenoxyethanol and Sodium Methylparaben, Merck; Eutanol® G, INCI: Octyldodecanol, Cognis GmbH; Eutanol® G 16, INCI: Hexyldecanol, Cognis GmbH; Eutanol® G 16 S, INCI: Hexyldecyl Stearate, Cognis GmbH; Finsolv® TN, INCI: C 12/15 Alkyl Benzoate, Findex (Nordmann/Rassmann); Fitoderm®, INCI Squalane, Cognis GmbH; Generol® R, INCI: Brassica Campestris (Rapseed) Sterols, Cognis GmbH; Glucate® DO, INCI: Methyl Glucose Dioleate, NRC Nordmann/Rassmann; Hispagel® 200, INCI: Glycerin, Glyceryl Polyacrylate, Cognis GmbH; Hostaphat® KL 340 N, INCI: Trilaureth-4 Phosphate, Clariant; Hydagen® C.A.T., INCI Triethyl Citrate, Cognis GmbH; Hydagen® DCMF, INCI: Chitosan, Cognis GmbH; Insect Repellent® 3535, INCI: Ethyl Butylacetylaminopropionate, EMD Chemicals Inc; Isolan® PDI, INCI: Diisostearoyl Polyglyceryl-3 Diisostearate, Goldschmidt AG; Isolan® GPS, INCI: Polyglyceryl-4 Diisostearate/Polyhydroxystearate/Sebacate, Evonik Goldschmidt; Isolan® GI 34, INCI: Polyglyceryl-4 Isostearate, Evonik Goldschmidt; Irwinol® LS 9319, INCI: Octyldecanol, Irvingia Gabonensis Kernel Butter, Hydrogenated Coco-Glycerides, Keltrol®, INCI: Xanthan Gum, CP Kelco; Lameform® TGI, INCI: Polyglyceryl-3 Diisostearate, Cognis GmbH; Lanette® 14, INCI: Myristyl Alcohol, Cognis GmbH; Lanette® 18, INCI: Stearyl Alcohol, Cognis GmbH; Lanette® 22, INCI: Behenyl Alcohol, Cognis GmbH; Lanette® E, INCI: Sodium Cetearyl Sulfate, Cognis GmbH; Lanette® O, INCI: Cetearyl Alcohol, Cognis GmbH; Locron® L, INCI: Aluminium Chlorhydrate, Clariant; Locentite® SAN, INCI: Quaternium-18 Hectorit, Co-Op Chemical Co., Ltd.; Microna® Matte White ((INCI: Titanium Dioxide, Zinc Oxide); Microna® Matte Black (INCI: Iron Oxide; Mica); Microna® Matte Yellow (INCI: Iron Oxide; Mica); Microna® Matte Red (INCI: Iron Oxide; Mica), Cosmetic white C47056 (INCI: Titanium Dioxide, Mica); FDC Yellow 6 Al Lake C705270 (INCI: Colour Index 15985); DC Red 7 Ca Lake C 19003 (INCI: Colour Index 15850); Irodin 100 Silverpearl, (INCI; Mica, Titanium dioxide); Colophane Claire type Y (INCI: Colophonium); Mononauls® 90-O 18, INCI: Glyceryl Oleate, Cognis GmbH; Monomuls® 90 L 12, INCI: Glyceryl Laurate, Cognis GmbH; Myrj® 51, INCI: PEG-30-Sterate, Uniqema; Myritol® 312, INCI: Caprylic/Capric Triglyceride, Cognis GmbH; Myritol® 331, Cocoglycerides, Cognis GmbH; Myritol® PC, INCI: PropyleneGlycol Dicaprylate/Dicaprate, Cognis GmbH; Neo Heliopan® 303, INCI: Octocrylene, Symrise; Neo Heliopan® AP, INCI: Disodium Phenyl Dibenzimidazole Tetrasulfonate, Symrise; Neo Heliopa® AV, INCI: Ethylhexyl Methoxycinnamate, Symrise; Neo Heliopan® BB, INCI: Benzophenone-3, Symrise; Neo Heliopan® E 1000, INCI: Isoamyl-p-Methoxycinnamate, Symrise; Neo Heliopan® Hydro, Phenylbenzimidazole Sulfonic Acid, Symrise; Nee Heliopan® MBC, INCI: 4-Methylbenzylidene Camphor, Symrise; Neo Heliopan® OS, INCI: Ethylhexyl Salicylate, Symrise; Novata® AB, INCI: Cocoglycerides, Cognis GmbH; Parsol® 1789, INCI: Butyl Methoxydibenzoylmethane, Hoffmann-La Roche (Givaudan); Pemulcn® TR-2 Polymer, INCI: Acrylates/C10-30 Alkylacrylate Crosspolymer, Noveon, Inc.; Photony® LS, INCI: Arginine, Disodium Adenosine Triphosphate, Mannitol, Pyridoxine HCL, Phenylalanine, Tyrosine, Laboratoires Serobiologiques (Cognis); Prisorine® 3505, INCI: Isostearic Acid; Uniqema; Prisorine® 3758, INCI; Hydrogenated Polyisobutene, Uniqema; Rezal 360, INCI: Aluminum Zirconium Tetrachlorohydrex GLY Reheis, Inc; Rheocare® C Plus, INCI Carbomer, Cognis GmbH; Ronasphere® LDP, INCI: Silica, Titaniumdioxide, Iron Oxides; Squatol® 5, INCI: Hydrogenated Polyisobutene, BASF Corp.; Poloxamer® 101, INCI: Poloxamer, BASF SE; SFE® 839, INCI: Cyclopentasiloxane and Dimethicone/Vinyl Dimethicone Crosspolymer, GE Silicones; Silicone oil Wacker AK® 350, INCI: Dimethicone, Wacker; Tego® Care 450, INCI: Polyglyceryl-3 Methylglucose Distearate, Goldschmidt; Tego® Care CG 90, INCI: Cetearyl Glucoside, Goldschmidt; Tegosoft® DEC, INCI: Diethylhexyl Carbonate, Goldschmidt; Tinosorb® S, Bis-Ethylhexyloxyphenol Methoxyphenyl Triazine; Ciba Specialty Chemicals Corporation; Tinosorb® M, INCI: Methylene Bis-Benzotriazolyl Tetramethylbutylphenol, Ciba Specialty Chemicals Corporation; Tween® 60, INCI: Polysorbate 60, Uniqema (ICI Surfactants), Uvasorb® HEB, INCI: Diethylhexyl Butamido Triazone, 3V Inc.; Unirep® U-18, INCI: Dimethyl Phthalate and Diethyl Toluamide and Ethyl Hexanediol, Induchem AU; Uvinul® T 150, INCI: Ethylhexyl Triazone, BASF; Uvinul® A plus, INCI: Diethylamino Hydroxybenzoyl Hexyl Benzoate, BASF; Veegum® Ultra, INCI: Magnesium Aluminium Silicate, R. T. Vanderbilt Company, Inc; Veegum® Plus, INCI: Magnesium Aluminum Silicate and Cellulose Gum, R. T. Vanderbilt Company, Inc; Z-Cote® HP 1, INCI: Zinc Oxide and Triethoxy-caprylylsilane, BASF, Zinc Oxide NDM, INCI: Zinc Oxide, Symrise.

The invention claimed is:

1. A cosmetic and/or pharmaceutical composition comprising 0.1 to 95% by weight of an ester of the general formula (I)

$$R_1-C(=O)-O-R_2$$

wherein
(a) $R_1$ is a linear alkyl radical having 7 to 9 carbon atoms and $R_2$ is a linear alkyl radical having 9 to 10 carbon atoms, or
(b) $R_1$ is a linear alkyl radical having 8 to 9 carbon atoms and $R_2$ is a linear alkyl radical having 8 carbon atoms, or
(c) $R_1$ is a linear alkyl radical having 7 to 9 carbon atoms and $R_2$ is a linear alkyl radical having 7 carbon atoms
wherein the cosmetic and/or pharmaceutical composition does not contain a silicone.

2. The composition of claim 1 further comprising at least one interface-active substance and/or wax component and/or polymer and/or oil body.

3. The composition of claim 1 further comprising at least one UV photoprotective filter.

4. The composition of claim 1, wherein
a) the ester is at least one ester selected from the group consisting of at least one ester selected from the group consisting of n-nonyl n-octanoate, n-nonyl n-nonanoate, n-nonyl n-decanoate, n-decyl n-octanoate, n-decyl n-nonanoate, n-decyl n-decanoate, n-octyl n-nonanoate, n-octyl n-decanoate, n-heptyl n-octanoate, n-heptyl n-nonanoate, n-heptyl n-decanoate, and
b) the composition further comprises at least one emulsifier and/or surfactant and/or wax component and/or polymer and/or an oil body.

5. The composition of claim 1 which is impregnated or coated on a utility wipe or a hygiene wipe for cleaning the body and/or for bodycare.

6. The composition of claim 5, wherein the utility wipe or hygiene wipe is selected from the group consisting of tissues, papers, nonwoven products, sponges, puffs, plasters and bandages.

7. The composition of claim 1, wherein the composition comprises 0.2 to 80% by weight, 0.5 to 70% by weight, 0.75 to 60% by weight, 1 to 50% by weight, or 1-40% by weight, of at the at least one ester (a).

8. The composition of claim 7, further comprising 0.1-20% by weight of the interface-active substance and/or wax component and/or polymer, 0.1-40% by weight of further oil bodies and 0-98% by weight of water.

9. A method for improving lightness, non-greasy skin feel, softness, spreadability, absorption, distributability, or oiliness of a cosmetic and/or pharmaceutical composition comprising incorporating into the composition 0.1 to 95% by weight of an ester of the general formula (I)

$$R_1-C(=O)-O-R_2$$

wherein
(a) $R_1$ is a linear alkyl radical having 7 to 9 carbon atoms and $R_2$ is a linear alkyl radical having 9 to 10 carbon atoms, or
(b) $R_1$ is a linear alkyl radical having 8 to 9 carbon atoms and $R_2$ is a linear alkyl radical having 8 carbon atoms, or
(c) $R_1$ is a linear alkyl radical having 7 to 9 carbon atoms and $R_2$ is a linear alkyl radical having 7 carbon atoms
wherein the cosmetic and/or pharmaceutical composition does not contain a silicone.

* * * * *